US012697207B2

(12) United States Patent
Guttenberg et al.

(10) Patent No.: US 12,697,207 B2
(45) Date of Patent: Aug. 4, 2026

(54) EXPANDABLE SURGICAL HEART VALVE INDICATORS

(71) Applicant: Edwards Lifesciences Corporation, Irvine, CA (US)

(72) Inventors: Jessica Guttenberg, Irvine, CA (US); Da-Yu Chang, Irvine, CA (US); Derrick Johnson, Orange, CA (US); Brian S. Conklin, Orange, CA (US); Qinggang Zeng, Mission Viejo, CA (US); Myron Howanec, Jr., Corona, CA (US); Grace Myong Kim, Seal Beach, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 1188 days.

(21) Appl. No.: 17/508,893

(22) Filed: Oct. 22, 2021

(65) Prior Publication Data

US 2022/0039945 A1     Feb. 10, 2022

Related U.S. Application Data

(63) Continuation of application No. 16/270,849, filed on Feb. 8, 2019, now Pat. No. 11,154,394, which is a
(Continued)

(51) Int. Cl.
*A61F 2/24* (2006.01)

(52) U.S. Cl.
CPC .......... *A61F 2/2418* (2013.01); *A61F 2/2409* (2013.01); *A61F 2/2412* (2013.01);
(Continued)

(58) Field of Classification Search
CPC ........ A61F 2/24; A61F 2/2409; A61F 2/2418; A61F 2/2412; A61F 2/2415; A61F 2/2496
See application file for complete search history.

(56) References Cited

U.S. PATENT DOCUMENTS

| | | | |
|---|---|---|---|
| 30,912 | A | 12/1860 | Hancock |
| 3,143,742 | A | 8/1964 | Cromie |

(Continued)

FOREIGN PATENT DOCUMENTS

| | | |
|---|---|---|
| EP | 0125393 A1 | 11/1984 |
| EP | 0143246 A2 | 6/1985 |

(Continued)

OTHER PUBLICATIONS

Bapat, et al., "Fluoroscopic Guide to an Ideal Implant Position for Sapien XT and CoreValve During a Valve-in-Valve Procedure", Cardiovascular Interventions, vol. 6, No. 11, 2013, Published by Elsevier Inc., London, United Kindgom, 9 pages.
(Continued)

*Primary Examiner* — William H Matthews
(74) *Attorney, Agent, or Firm* — Guy Cumberbatch

(57) ABSTRACT

A prosthetic heart valve configured to replace a native heart valve and for post-implant expansion and having a valve-type indicator thereon visible from outside the body post-implant. The indicator communicates information about the valve, such as the size or orifice diameter of the valve, and/or that the valve has the capacity for post-implant expansion. The indicator can be an alphanumeric symbol or other symbol or combination of symbols that represent information about the characteristics of the valve such as the valve size. The capacity for post-implant expansion facilitates a valve-in-valve procedure, where the valve-type indicator conveys information to the surgeon about whether the implanted valve is suitable for the procedure and informs the choice of the secondary valve.

23 Claims, 9 Drawing Sheets

Related U.S. Application Data continuation of application No. 29/579,402, filed on Sep. 29, 2016, now Pat. No. Des. 867,594, which is a continuation-in-part of application No. 14/745,287, filed on Jun. 19, 2015, now Pat. No. 9,504,566.

(60) Provisional application No. 62/015,290, filed on Jun. 20, 2014.

(52) U.S. Cl.
CPC .......... *A61F 2/2472* (2013.01); *A61F 2/2427* (2013.01); *A61F 2250/0085* (2013.01); *A61F 2250/0089* (2013.01); *A61F 2250/0098* (2013.01)

(56) References Cited

U.S. PATENT DOCUMENTS

| | | | |
|---|---|---|---|
| 3,320,972 A | 5/1967 | High et al. | |
| 3,371,352 A | 3/1968 | Siposs et al. | |
| 3,546,710 A | 12/1970 | Shumakov et al. | |
| 3,574,865 A | 4/1971 | Hamaker | |
| 3,755,823 A | 9/1973 | Hancock | |
| 3,839,741 A | 10/1974 | Haller | |
| 3,997,923 A | 12/1976 | Possis | |
| 4,035,849 A | 7/1977 | Angell et al. | |
| 4,078,468 A | 3/1978 | Civitello | |
| 4,079,468 A | 3/1978 | Liotta et al. | |
| 4,084,268 A | 4/1978 | Ionescu et al. | |
| 4,106,129 A | 8/1978 | Carpentier et al. | |
| 4,172,295 A | 10/1979 | Batten | |
| 4,217,665 A | 8/1980 | Bex et al. | |
| 4,218,782 A | 8/1980 | Rygg | |
| 4,259,753 A | 4/1981 | Liotta et al. | |
| RE30,912 E | 4/1982 | Ende | |
| 4,340,091 A | 7/1982 | Skelton et al. | |
| 4,343,048 A | 8/1982 | Ross et al. | |
| 4,364,126 A | 12/1982 | Rosen et al. | |
| 4,388,735 A | 6/1983 | Ionescu et al. | |
| 4,441,216 A | 4/1984 | Ionescu et al. | |
| 4,451,936 A | 6/1984 | Carpentier et al. | |
| 4,470,157 A | 9/1984 | Love | |
| 4,490,859 A | 1/1985 | Black et al. | |
| 4,501,030 A | 2/1985 | Lane | |
| 4,506,394 A | 3/1985 | Bedard | |
| 4,535,483 A | 8/1985 | Klawitter et al. | |
| 4,566,465 A | 1/1986 | Arhan et al. | |
| 4,605,407 A | 8/1986 | Black et al. | |
| 4,626,255 A | 12/1986 | Reichart et al. | |
| 4,629,459 A | 12/1986 | Ionescu et al. | |
| 4,680,031 A | 7/1987 | Alonso | |
| 4,687,483 A | 8/1987 | Fisher | |
| 4,705,516 A | 11/1987 | Barone et al. | |
| 4,725,274 A | 2/1988 | Lane et al. | |
| 4,731,074 A | 3/1988 | Rousseau et al. | |
| 4,778,461 A | 10/1988 | Pietsch et al. | |
| 4,790,843 A | 12/1988 | Carpentier et al. | |
| 4,851,000 A | 7/1989 | Gupta | |
| 4,863,470 A * | 9/1989 | Carter ....................... A61F 2/12 623/8 |
| 4,888,009 A | 12/1989 | Lederman et al. | |
| 4,914,097 A | 4/1990 | Oda et al. | |
| 4,960,424 A | 10/1990 | Grooters | |
| 4,993,428 A | 2/1991 | Arms | |
| 5,010,892 A | 4/1991 | Colvin et al. | |
| 5,032,128 A | 7/1991 | Alonso | |
| 5,037,434 A | 8/1991 | Lane | |
| 5,147,391 A | 9/1992 | Lane | |
| 5,163,955 A | 11/1992 | Love et al. | |
| 5,258,023 A | 11/1993 | Reger | |
| 5,316,016 A | 5/1994 | Adams et al. | |
| 5,326,370 A | 7/1994 | Love et al. | |
| 5,326,371 A | 7/1994 | Love et al. | |
| 5,332,402 A | 7/1994 | Teitelbaum | |
| 5,360,014 A | 11/1994 | Sauter et al. | |
| 5,360,444 A | 11/1994 | Kusuhara | |
| 5,376,112 A | 12/1994 | Duran | |
| 5,396,887 A | 3/1995 | Imran | |
| 5,397,351 A | 3/1995 | Pavonik et al. | |
| 5,423,887 A | 6/1995 | Love et al. | |
| 5,425,741 A | 6/1995 | Lemp et al. | |
| 5,431,676 A | 7/1995 | Dubrul et al. | |
| 5,449,384 A | 9/1995 | Johnson | |
| 5,449,385 A | 9/1995 | Religa et al. | |
| 5,469,868 A | 11/1995 | Reger | |
| 5,488,789 A | 2/1996 | Religa et al. | |
| 5,489,296 A | 2/1996 | Love et al. | |
| 5,489,297 A | 2/1996 | Duran | |
| 5,489,298 A | 2/1996 | Love et al. | |
| 5,500,016 A | 3/1996 | Fisher | |
| 5,533,515 A | 7/1996 | Coller et al. | |
| 5,549,665 A | 8/1996 | Vesely et al. | |
| 5,562,729 A | 10/1996 | Purdy et al. | |
| 5,571,215 A | 11/1996 | Sterman et al. | |
| 5,573,007 A | 11/1996 | Bobo, Sr. | |
| 5,578,076 A | 11/1996 | Krueger et al. | |
| 5,584,803 A | 12/1996 | Stevens et al. | |
| 5,618,307 A | 4/1997 | Donlon et al. | |
| 5,626,607 A | 5/1997 | Malecki et al. | |
| 5,628,789 A | 5/1997 | Vanney et al. | |
| 5,693,090 A | 12/1997 | Unsworth et al. | |
| 5,695,503 A | 12/1997 | Krueger et al. | |
| 5,713,952 A | 2/1998 | Vanney et al. | |
| 5,716,370 A | 2/1998 | Williamson, IV et al. | |
| 5,728,064 A | 3/1998 | Burns et al. | |
| 5,728,151 A | 3/1998 | Garrison et al. | |
| 5,735,894 A | 4/1998 | Krueger et al. | |
| 5,752,522 A | 5/1998 | Murphy | |
| 5,755,782 A | 5/1998 | Love et al. | |
| 5,766,240 A | 6/1998 | Johnson | |
| 5,800,527 A | 9/1998 | Jansen et al. | |
| 5,814,097 A | 9/1998 | Sterman et al. | |
| 5,814,098 A | 9/1998 | Hinnenkamp et al. | |
| 5,824,064 A | 10/1998 | Taheri | |
| 5,824,068 A | 10/1998 | Bugge | |
| 5,840,081 A | 11/1998 | Andersen et al. | |
| 5,848,969 A | 12/1998 | Panescu et al. | |
| 5,855,563 A | 1/1999 | Kaplan et al. | |
| 5,855,601 A | 1/1999 | Bessler et al. | |
| 5,855,801 A | 1/1999 | Lin et al. | |
| 5,861,028 A | 1/1999 | Angell | |
| 5,891,160 A | 4/1999 | Williamson, IV et al. | |
| 5,895,420 A | 4/1999 | Mirsch, II et al. | |
| 5,902,308 A | 5/1999 | Murphy | |
| 5,908,450 A | 6/1999 | Gross et al. | |
| 5,919,147 A | 7/1999 | Jain | |
| 5,921,934 A | 7/1999 | Teo | |
| 5,921,935 A | 7/1999 | Hickey | |
| 5,924,984 A | 7/1999 | Rao | |
| 5,935,163 A | 8/1999 | Gabbay | |
| 5,957,949 A | 9/1999 | Leonhardt et al. | |
| 5,972,004 A | 10/1999 | Williamson, IV et al. | |
| 5,984,959 A | 11/1999 | Robertson et al. | |
| 5,984,973 A | 11/1999 | Girard et al. | |
| 6,010,531 A | 1/2000 | Donlon et al. | |
| 6,022,374 A * | 2/2000 | Imran ....................... A61F 2/91 623/1.34 |
| 6,042,554 A | 3/2000 | Rosenman et al. | |
| 6,042,607 A | 3/2000 | Williamson, IV et al. | |
| 6,048,362 A | 4/2000 | Berg | |
| 6,066,160 A | 5/2000 | Colvin et al. | |
| 6,074,418 A | 6/2000 | Buchanan et al. | |
| 6,081,737 A | 6/2000 | Shah | |
| 6,099,475 A | 8/2000 | Seward et al. | |
| 6,106,550 A | 8/2000 | Magovern et al. | |
| 6,110,200 A | 8/2000 | Hinnenkamp | |
| 6,117,091 A | 9/2000 | Young et al. | |
| 6,126,007 A | 10/2000 | Kari et al. | |
| 6,162,233 A | 12/2000 | Williamson, IV et al. | |
| 6,168,614 B1 | 1/2001 | Andersen et al. | |
| 6,176,877 B1 | 1/2001 | Buchanan et al. | |
| 6,197,054 B1 | 3/2001 | Hamblin, Jr. et al. | |
| 6,217,611 B1 | 4/2001 | Klostermeyer | |
| 6,231,561 B1 | 5/2001 | Frazier et al. | |

(56) References Cited

U.S. PATENT DOCUMENTS

| | | |
|---|---|---|
| 6,241,765 B1 | 6/2001 | Griffin et al. |
| 6,245,102 B1 | 6/2001 | Jayaraman |
| 6,264,611 B1 | 7/2001 | Ishikawa et al. |
| 6,283,127 B1 | 9/2001 | Sterman et al. |
| 6,287,339 B1 | 9/2001 | Vazquez et al. |
| 6,290,674 B1 | 9/2001 | Roue et al. |
| 6,312,447 B1 | 11/2001 | Grimes |
| 6,312,465 B1 | 11/2001 | Griffin et al. |
| 6,328,727 B1 | 12/2001 | Frazier et al. |
| 6,350,282 B1 | 2/2002 | Eberhardt |
| 6,361,557 B1 * | 3/2002 | Gittings .................. A61F 2/07 |
| | | 606/151 |
| 6,371,983 B1 | 4/2002 | Lane |
| 6,375,620 B1 | 4/2002 | Oser et al. |
| 6,402,780 B2 | 6/2002 | Williamson, IV et al. |
| 6,425,916 B1 | 7/2002 | Garrison et al. |
| 6,440,164 B1 | 8/2002 | Di Matteo et al. |
| 6,454,799 B1 | 9/2002 | Schreck |
| 6,458,153 B1 | 10/2002 | Bailey et al. |
| 6,468,305 B1 | 10/2002 | Otte |
| 6,491,624 B1 | 12/2002 | Lotfi |
| 6,582,462 B1 | 6/2003 | Andersen et al. |
| 6,582,464 B2 | 6/2003 | Gabbay |
| 6,585,766 B1 | 7/2003 | Huynh et al. |
| 6,613,087 B1 | 9/2003 | Healy et al. |
| 6,652,578 B2 | 11/2003 | Bailey et al. |
| 6,682,559 B2 | 1/2004 | Myers et al. |
| 6,685,739 B2 | 2/2004 | DiMatteo et al. |
| 6,730,118 B2 | 5/2004 | Spenser et al. |
| 6,733,525 B2 | 5/2004 | Yang et al. |
| 6,764,508 B1 | 7/2004 | Roehe et al. |
| 6,767,362 B2 | 7/2004 | Schreck |
| 6,773,457 B2 | 8/2004 | Ivancev et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,805,711 B2 | 10/2004 | Quijano et al. |
| 6,893,459 B1 | 5/2005 | Macoviak |
| 6,893,460 B2 | 5/2005 | Spenser et al. |
| 6,908,481 B2 | 6/2005 | Cribier |
| 6,939,365 B1 | 9/2005 | Fogarty et al. |
| 7,011,681 B2 | 3/2006 | Vesely |
| 7,018,404 B2 | 3/2006 | Holmberg et al. |
| 7,025,780 B2 | 4/2006 | Gabbay |
| 7,070,616 B2 | 7/2006 | Majercak et al. |
| 7,097,659 B2 | 8/2006 | Woolfson et al. |
| 7,101,396 B2 | 9/2006 | Artof et al. |
| 7,137,184 B2 | 11/2006 | Schreck |
| 7,147,663 B1 | 12/2006 | Berg et al. |
| 7,153,324 B2 | 12/2006 | Case et al. |
| 7,195,641 B2 | 3/2007 | Palmaz et al. |
| 7,201,771 B2 | 4/2007 | Lane |
| 7,201,772 B2 | 4/2007 | Schwammenthal et al. |
| 7,238,200 B2 | 7/2007 | Lee et al. |
| 7,247,167 B2 | 7/2007 | Gabbay |
| 7,252,682 B2 | 8/2007 | Seguin |
| 7,261,732 B2 | 8/2007 | Justino |
| 7,333,013 B2 | 2/2008 | Berger |
| RE40,377 E | 6/2008 | Williamson, IV et al. |
| 7,422,603 B2 | 9/2008 | Lane |
| 7,474,223 B2 | 1/2009 | Nycz et al. |
| 7,513,909 B2 | 4/2009 | Lane et al. |
| 7,556,647 B2 | 7/2009 | Drews et al. |
| 7,569,072 B2 | 8/2009 | Berg et al. |
| 7,947,022 B2 | 5/2011 | Amin et al. |
| 7,998,151 B2 | 8/2011 | St. Goar et al. |
| 8,075,536 B2 | 12/2011 | Gray et al. |
| 8,784,481 B2 | 7/2014 | Alkhatib et al. |
| 8,845,720 B2 | 9/2014 | Conklin |
| 8,998,981 B2 | 4/2015 | Tuval et al. |
| 9,089,422 B2 | 7/2015 | Ryan et al. |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0049492 A1 | 12/2001 | Frazier et al. |
| 2002/0020074 A1 | 2/2002 | Love et al. |
| 2002/0026238 A1 | 2/2002 | Lane et al. |
| 2002/0032481 A1 | 3/2002 | Gabbay |
| 2002/0058995 A1 | 5/2002 | Stevens |
| 2002/0123802 A1 | 9/2002 | Snyders |
| 2002/0138138 A1 | 9/2002 | Yang |
| 2002/0151970 A1 | 10/2002 | Garrison et al. |
| 2002/0188348 A1 | 12/2002 | DiMatteo et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0036795 A1 | 2/2003 | Andersen et al. |
| 2003/0040792 A1 | 2/2003 | Gabbay |
| 2003/0055495 A1 | 3/2003 | Pease et al. |
| 2003/0055496 A1 | 3/2003 | Cai et al. |
| 2003/0105519 A1 | 6/2003 | Fasol et al. |
| 2003/0109924 A1 | 6/2003 | Cribier |
| 2003/0114913 A1 | 6/2003 | Spenser et al. |
| 2003/0130729 A1 | 7/2003 | Paniagua et al. |
| 2003/0149478 A1 | 8/2003 | Figulla et al. |
| 2003/0167089 A1 | 9/2003 | Lane |
| 2003/0236568 A1 | 12/2003 | Hojeibane et al. |
| 2004/0019374 A1 | 1/2004 | Hojeibane et al. |
| 2004/0034411 A1 | 2/2004 | Quijano et al. |
| 2004/0044406 A1 | 3/2004 | Woolfson et al. |
| 2004/0106976 A1 | 6/2004 | Bailey et al. |
| 2004/0122514 A1 | 6/2004 | Fogarty et al. |
| 2004/0122516 A1 | 6/2004 | Fogarty et al. |
| 2004/0167573 A1 | 8/2004 | Williamson et al. |
| 2004/0167619 A1 | 8/2004 | Case et al. |
| 2004/0186563 A1 | 9/2004 | Iobbi |
| 2004/0186565 A1 | 9/2004 | Schreck |
| 2004/0193261 A1 | 9/2004 | Berreklouw |
| 2004/0206363 A1 | 10/2004 | McCarthy et al. |
| 2004/0210304 A1 | 10/2004 | Seguin et al. |
| 2004/0210307 A1 | 10/2004 | Khairkhahan |
| 2004/0225355 A1 | 11/2004 | Stevens |
| 2004/0236411 A1 | 11/2004 | Sarac et al. |
| 2004/0260389 A1 | 12/2004 | Case et al. |
| 2004/0260390 A1 | 12/2004 | Sarac et al. |
| 2005/0010285 A1 | 1/2005 | Lambrecht et al. |
| 2005/0027348 A1 | 2/2005 | Case et al. |
| 2005/0033398 A1 | 2/2005 | Seguin |
| 2005/0043760 A1 | 2/2005 | Fogarty et al. |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065614 A1 | 3/2005 | Stinson |
| 2005/0075584 A1 | 4/2005 | Cali |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0080454 A1 | 4/2005 | Drews et al. |
| 2005/0096738 A1 | 5/2005 | Call et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137690 A1 | 6/2005 | Salahieh et al. |
| 2005/0137692 A1 | 6/2005 | Haug et al. |
| 2005/0137695 A1 | 6/2005 | Salahieh et al. |
| 2005/0159811 A1 | 7/2005 | Lane |
| 2005/0165479 A1 | 7/2005 | Drews et al. |
| 2005/0182486 A1 | 8/2005 | Gabbay |
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0216079 A1 | 9/2005 | MaCoviak |
| 2005/0222674 A1 | 10/2005 | Paine |
| 2005/0234546 A1 | 10/2005 | Nugent et al. |
| 2005/0240263 A1 | 10/2005 | Fogarty et al. |
| 2005/0251252 A1 | 11/2005 | Stobie |
| 2005/0261765 A1 | 11/2005 | Liddicoat |

(56)  References Cited

U.S. PATENT DOCUMENTS

| | | |
|---|---|---|
| 2005/0283231 A1 | 12/2005 | Haug et al. |
| 2006/0008497 A1 | 1/2006 | Gabbay |
| 2006/0025857 A1 | 2/2006 | Bergheim et al. |
| 2006/0052867 A1 | 3/2006 | Revuelta et al. |
| 2006/0058871 A1 | 3/2006 | Zakay et al. |
| 2006/0058872 A1 | 3/2006 | Salahieh et al. |
| 2006/0074484 A1 | 4/2006 | Huber |
| 2006/0085060 A1 | 4/2006 | Campbell |
| 2006/0095125 A1 | 5/2006 | Chinn et al. |
| 2006/0122634 A1 | 6/2006 | Ino et al. |
| 2006/0149360 A1 | 7/2006 | Schwammenthal et al. |
| 2006/0154230 A1 | 7/2006 | Cunanan et al. |
| 2006/0167543 A1 | 7/2006 | Bailey et al. |
| 2006/0195184 A1 | 8/2006 | Lane et al. |
| 2006/0195185 A1 | 8/2006 | Lane et al. |
| 2006/0195186 A1 | 8/2006 | Drews et al. |
| 2006/0207031 A1 | 9/2006 | Cunanan et al. |
| 2006/0228263 A1 | 10/2006 | Berndtsson |
| 2006/0259136 A1 | 11/2006 | Nguyen et al. |
| 2006/0271172 A1 | 11/2006 | Tehrani |
| 2006/0271175 A1 | 11/2006 | Woolfson et al. |
| 2006/0276813 A1 | 12/2006 | Greenberg |
| 2006/0287717 A1 | 12/2006 | Rowe et al. |
| 2006/0287719 A1 | 12/2006 | Rowe et al. |
| 2007/0010876 A1 | 1/2007 | Salahieh et al. |
| 2007/0016285 A1 | 1/2007 | Lane et al. |
| 2007/0016286 A1 | 1/2007 | Herrmann et al. |
| 2007/0016288 A1 | 1/2007 | Gurskis et al. |
| 2007/0043435 A1 | 2/2007 | Seguin et al. |
| 2007/0078509 A1 | 4/2007 | Lotfy |
| 2007/0078510 A1 | 4/2007 | Ryan |
| 2007/0100440 A1 | 5/2007 | Figulla et al. |
| 2007/0129794 A1 | 6/2007 | Realyvasquez |
| 2007/0142906 A1 | 6/2007 | Figulla et al. |
| 2007/0142907 A1 | 6/2007 | Moaddeb et al. |
| 2007/0150053 A1 | 6/2007 | Gurskis et al. |
| 2007/0156233 A1 | 7/2007 | Kapadia et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0179604 A1 | 8/2007 | Lane |
| 2007/0185565 A1 | 8/2007 | Schwammenthal et al. |
| 2007/0198097 A1 | 8/2007 | Zegdi |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0225801 A1 | 9/2007 | Drews et al. |
| 2007/0233237 A1 | 10/2007 | Krivoruchko |
| 2007/0238979 A1 | 10/2007 | Huynh et al. |
| 2007/0239266 A1 | 10/2007 | Birdsall |
| 2007/0239269 A1 | 10/2007 | Dolan et al. |
| 2007/0239273 A1 | 10/2007 | Allen |
| 2007/0255398 A1 | 11/2007 | Yang et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0282436 A1 | 12/2007 | Pinchuk |
| 2007/0288089 A1 | 12/2007 | Gurskis et al. |
| 2008/0033543 A1 | 2/2008 | Gurskis et al. |
| 2008/0039934 A1 | 2/2008 | Styrc |
| 2008/0071369 A1 | 3/2008 | Tuval et al. |
| 2008/0119875 A1 | 5/2008 | Ino et al. |
| 2008/0154356 A1 | 6/2008 | Obermiller et al. |
| 2008/0200977 A1* | 8/2008 | Paul ..................... A61F 2/2475 623/1.24 |
| 2008/0319543 A1 | 12/2008 | Lane |
| 2009/0036903 A1 | 2/2009 | Ino et al. |
| 2009/0054973 A1* | 2/2009 | Johnson ................ A61F 2/2412 623/2.38 |
| 2009/0138079 A1 | 5/2009 | Tuval et al. |
| 2009/0156928 A1 | 6/2009 | Evans et al. |
| 2009/0192591 A1* | 7/2009 | Ryan ..................... A61F 2/2436 623/2.11 |
| 2009/0192599 A1 | 7/2009 | Lane et al. |
| 2009/0264989 A1 | 10/2009 | Bonhoeffer et al. |
| 2010/0049313 A1 | 2/2010 | Alon et al. |
| 2010/0168839 A1 | 7/2010 | Braido et al. |
| 2010/0185277 A1 | 7/2010 | Braido et al. |
| 2010/0249923 A1 | 9/2010 | Alkhatib et al. |
| 2010/0298931 A1 | 11/2010 | Quadri et al. |
| 2011/0034802 A1 | 2/2011 | Shrivastava et al. |
| 2012/0065503 A1 | 3/2012 | Rogers et al. |
| 2014/0163673 A1 | 6/2014 | Bruchman et al. |
| 2014/0188221 A1 | 7/2014 | Chung |
| 2014/0343670 A1 | 11/2014 | Bakis et al. |
| 2015/0018944 A1 | 1/2015 | O'Connell et al. |
| 2016/0296324 A1 | 10/2016 | Bapat et al. |
| 2018/0021554 A1 | 1/2018 | Nebosky et al. |

FOREIGN PATENT DOCUMENTS

| | | |
|---|---|---|
| EP | 1239795 B1 | 12/2006 |
| JP | H1189940 A | 4/1999 |
| SU | 1116573 A1 | 7/1985 |
| SU | 1697790 A1 | 12/1991 |
| WO | 9213502 A1 | 8/1992 |
| WO | 9742871 A1 | 11/1997 |
| WO | 2009106545 A1 | 9/2009 |
| WO | 2010019781 A1 | 2/2010 |
| WO | 2010019781 | 5/2011 |
| WO | 2012018779 A2 | 2/2012 |
| WO | 2015073815 A1 | 5/2015 |

OTHER PUBLICATIONS

Bapat V.N., et al., "The Transcatheter Aortic Valve Implantation—TAVI—With Emphasis on the Use of the Edwards SAPIEN Pericardial Valve," The Pericardial Heart Valve, Chapter 3, The Odyssey of a Continuously Evolving Concept, Society for Cardiothoracic Surgery in Great Britain and Ireland, 2014, 29 Pages.

Noorani, et al., "Valve-in-valve procedure: importance of the anatomy of surgical bioprostheses," The Author 2014. Published by Oxford University Press on behalf of the European Association for Cardio-Thoracic Surgery.

Noorani, et al., "There's an App for That!," Cardiac Interventions Today Jul./Aug. 2014.

* cited by examiner

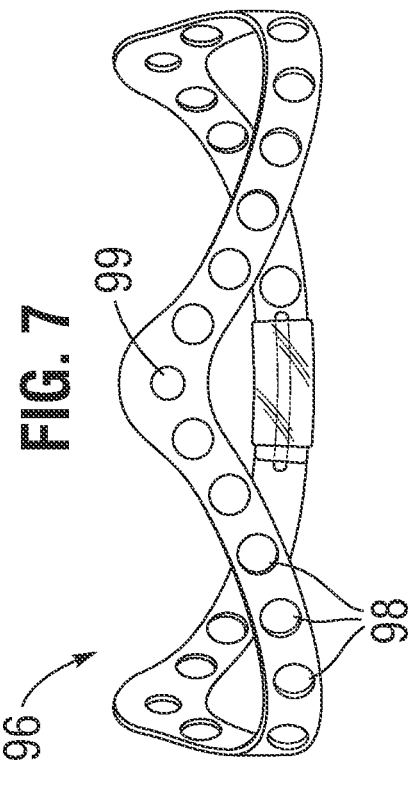
FIG. 7
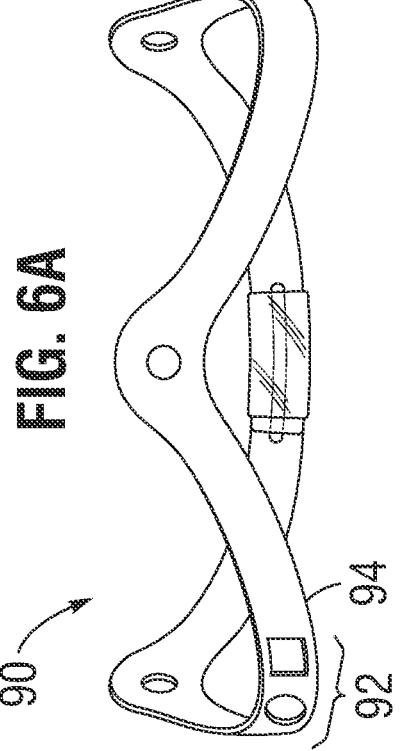
FIG. 6A
FIG. 6B
| 1st Position | | 2nd Position | |
|---|---|---|---|
| □ | → 1 | □ | → 1 |
| ○ | → 2 | ○ | → 3 |
| | | △ | → 5 |
| | | ☆ | → 7 |
| | | ✕ | → 9 |

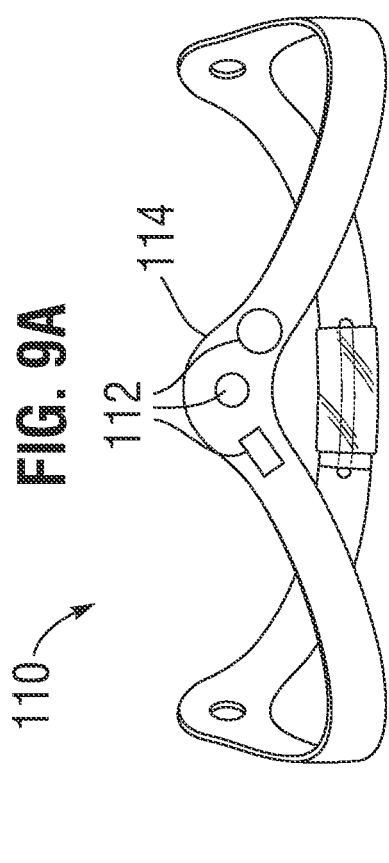
FIG. 9A
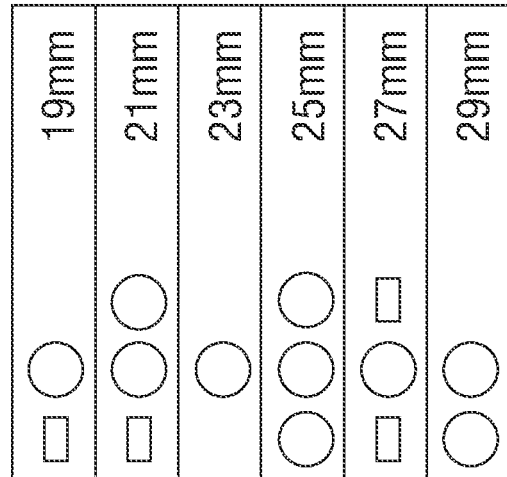
FIG. 9B
| 19mm | 21mm | 23mm | 25mm | 27mm | 29mm |
|---|---|---|---|---|---|
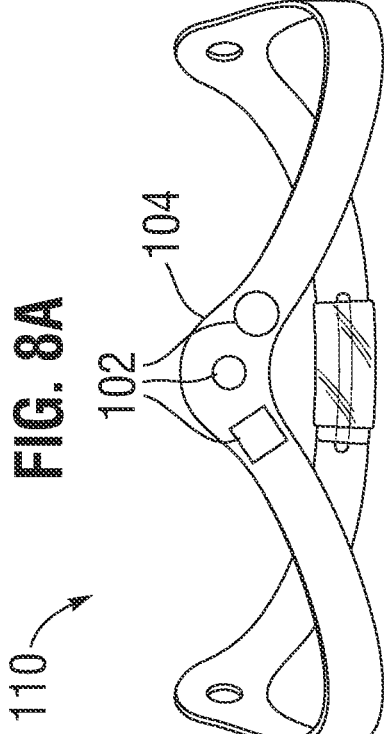
FIG. 8A
FIG. 8B
| 19mm | 21mm | 23mm | 25mm | 27mm | 29mm |
|---|---|---|---|---|---|

EXPANDABLE SURGICAL HEART VALVE INDICATORS

CROSS REFERENCE TO RELATED APPLICATIONS

This application is a continuation of U.S. patent application Ser. No. 16/270,849, filed Feb. 8, 2019, now U.S. Pat. No. 11,154,394, which is a continuation of U.S. patent application Ser. No. 29/579,402, filed Sep. 29, 2016, now U.S. Pat. No. D867,594, which is a continuation-in-part of U.S. patent application Ser. No. 14/745,287, filed Jun. 19, 2015, now U.S. Pat. No. 9,504,566, which claims the benefit of U.S. Patent Application No. 62/015,290, filed Jun. 20, 2014, the entire contents all of which are expressly incorporated by reference for all purposes.

TECHNICAL FIELD

This disclosure relates to a surgical heart valve for heart valve replacement and, more particularly, to surgical heart valves having indicators visible from outside the body post-implant.

BACKGROUND

The heart is a hollow muscular organ having four pumping chambers and four heart valves: aortic, mitral (or bicuspid), tricuspid, and pulmonary. Heart valves are comprised of a dense fibrous ring known as the annulus, and leaflets or cusps attached to the annulus.

Heart valve disease is a widespread condition in which one or more of the valves of the heart fails to function properly. Diseased heart valves may be categorized as either stenotic, wherein the valve does not open sufficiently to allow adequate forward flow of blood through the valve, and/or incompetent, wherein the valve does not close completely, causing excessive backward flow of blood through the valve when the valve is closed. Valve disease can be severely debilitating and even fatal if left untreated. Various surgical techniques may be used to replace or repair a diseased or damaged valve. In a traditional valve replacement operation, the damaged leaflets are typically excised and the annulus sculpted to receive a replacement prosthetic valve.

A surgical prosthetic heart valve typically comprises a support structure (such as a frame, ring and/or stent) with a valve assembly deployed therein. The support structure is often rigid, and can be formed of various biocompatible materials, including metals, plastics, ceramics, etc. Two primary types of heart valve replacements or prostheses are known. One is a mechanical-type heart valve that uses a ball and cage arrangement or a pivoting mechanical closure supported by a base structure to provide unidirectional blood flow, such as shown in U.S. Pat. No. 6,143,025 to Stobie, et al. and U.S. Pat. No. 6,719,790 to Brendzel, et al., the entire disclosures of which are hereby expressly incorporated by reference. The other is a tissue-type or "bioprosthetic" valve having flexible leaflets supported by a base structure and projecting into the flow stream that function much like those of a natural human heart valve and imitate their natural flexing action to coapt against each other and ensure one-way blood flow.

In tissue-type valves, a whole xenograft valve (e.g., porcine) or a plurality of xenograft leaflets (e.g., bovine pericardium) can provide fluid occluding surfaces. Synthetic leaflets have been proposed, and thus the term "flexible leaflet valve" refers to both natural and artificial "tissue-type" valves. In a typical tissue-type valve, two or more flexible leaflets are mounted within a peripheral support structure that usually includes posts or commissures extending in the outflow direction to mimic natural fibrous commissures in the native annulus. The metallic or polymeric "support frame," sometimes called a "wireform" or "stent," has a plurality (typically three) of large radius cusps supporting the cusp region of the flexible leaflets (e.g., either a whole xenograft valve or three separate leaflets). The ends of each pair of adjacent cusps converge somewhat asymptotically to form upstanding commissures that terminate in tips, each extending in the opposite direction as the arcuate cusps and having a relatively smaller radius. Components of the valve are usually assembled with one or more biocompatible fabric (e.g., Dacron® polyethylene terephthalate (PET)) coverings, and a fabric-covered sewing ring is provided on the inflow end of the peripheral support structure.

One example of the construction of a flexible leaflet valve is seen in U.S. Pat. No. 6,585,766 to Huynh, et al. (issued Jul. 1, 2003), in which the exploded view of FIG. 1 thereof illustrates a fabric-covered wireform 54 and a fabric-covered support stent 56 on either side of a leaflet subassembly 52. The contents of U.S. Pat. No. 6,585,766 are hereby incorporated by reference in their entirety. Other examples of valve and related assemblies/systems are found in U.S. Pat. No. 4,084,268, which issued Apr. 18, 1978; U.S. Pat. No. 7,137,184, which issued on Nov. 21, 2006; U.S. Pat. No. 8,308,798, filed Dec. 10, 2009; U.S. Pat. No. 8,348,998, filed Jun. 23, 2010; and U.S. Patent Publication No. 2012/0065729, filed Jun. 23, 2011; the entire contents of each of which are hereby incorporated by reference in their entirety.

Sometimes the need for complete valve replacement may arise after a patient has already had an earlier valve replacement for the same valve. For example, a prosthetic heart valve that was successfully implanted to replace a native valve may itself suffer damage and/or wear and tear many years after initially being implanted. Implanting the prosthetic heart valve directly within a previously-implanted prosthetic heart valve may be impractical, in part because the new prosthetic heart valve (including the support structure and valve assembly) will have to reside within the annulus of the previously-implanted heart valve, and traditional prosthetic heart valves may not be configured to easily receive such a valve-within-a-valve implantation in a manner which provides secure seating for the new valve while also having a large enough annulus within the new valve to support proper blood flow therethrough.

Some attention has been paid to the problem of implanting a new valve within an old valve. In particular, the following disclose various solutions for valve-in-valve systems: U.S. Patent Application Publication No. 2010/0076548 A1 to Konno, filed Sep. 19, 2008; and U.S. Pat. No. 8,613,765 to Bonhoeffer, filed Jul. 7, 2011.

Despite certain advances in the valve-in-valve area, there remains a need to quickly identify physical characteristics of a previously implanted heart valve, including whether a previously implanted surgical valve is suitable for a valve-in-valve procedure.

SUMMARY

The present application solves a number of problems related to identification of prosthetic heart valves post-implant. The heart valves have an indicator thereon visible from outside the body by an external imager, post-implant. The indicator communicates the size or orifice diameter of the surgical valve, and may also show that the valve has the capacity for post-implant expansion. It can also communicate other information, such as any combination of the manufacturer and/or model of the valve, the type of bio-prosthetic tissue or other material used to make the leaflets, and the valve's compatibility with other types of valves. The indicator may be an alphanumeric symbol and/or other symbol or symbols that represent, for example, the valve size number and/or other characteristic.

The present application discloses specific modifications to existing surgical valves that enable manufacturers to rapidly produce a valve which accommodates valve-in-valve (ViV) procedures. Specifically, some embodiments disclosed in the present application include retrofitting or modifying components within existing types of surgical valves to enable post-implant expansion.

In one embodiment of the present application, a prosthetic heart valve comprises an internal support frame defining a flow orifice therethrough and wherein the internal support frame is adapted for post-implant expansion. A plurality of flexible leaflets attaches to the support frame so as to extend across the flow orifice and come together within the orifice and provide one-way flow therethrough. The prosthetic heart valve further includes a valve-type indicator that provides information about a characteristic of the heart valve and is visible using an external imager. The valve-type indicator may signify the capability of the support frame for post-implant expansion of the orifice.

The prosthetic heart valve preferably has a labeled valve size, and the valve-type indicator comprises a valve-size indicator that denotes the labeled valve size and is visible or readable using an external imager. For example, the valve-size indicator comprises a numerical value that equals the labeled valve size in millimeters. In one embodiment, the internal support frame comprises a structural component that shows up as a positive image on the external imager, and the valve-type indicator is formed by one or more voids integrated into the structural component that show up as negative images on the external imager. For instance, the structural component of the internal support frame may be a generally tubular band that is adapted for post-implant expansion. In some embodiments, the valve-type indicator is integrated into a structural component to provide a positive image, for example as part of a band, stent, and/or wireframe.

In another embodiment, the valve-type indicator comprises an indicator element that shows up as a positive image on the external imager mounted to a structural component of the prosthetic heart valve that is not clearly visible to the external imager so that the valve-size indicator shows in contrast to the structural component on the external imager. For example, the structural component comprises a soft sealing ring surrounding an inflow end of the heart valve, and the indicator element is mounted to the sealing ring.

In one aspect, the prosthetic heart valve further includes an expandable tubular frame attached to an inflow end of the internal support frame on which the valve-size indicator is located. In such a configuration, the expandable tubular frame may have a series of circumferential and axial struts, wherein an upper strut is shaped with peaks and valleys around its periphery, and the valve-type indicator is integrated into the frame as a tag below the upper strut and along one of the axial struts. The expandable tubular frame is desirably metallic and is formed by laser cutting with the tag being the same material as the frame and formed during the laser cutting process.

In another embodiment, a prosthetic heart valve disclosed herein comprises an internal support frame defining a flow orifice therethrough, and a plurality of cusps that curve toward the inflow end separated by commissures. The support frame comprising an annular element disposed at an inflow end of the support frame that undulates so as to have peaks and valleys, with the peaks corresponding to the commissures of the support frame. A plurality of flexible leaflets attach to the support frame and extend across the flow orifice so as to come together within the orifice and ensure one-way flow therethrough, each of the leaflets attaching at a peripheral edge along the cusps and commissures of the support frame. An indicator is located on the annular element, for example, on at least one of the peaks or on at least one of the valleys of the annular element, that denotes a valve type and is visible or readable using an external imager.

In one form, the annular element includes a single expandable segment formed by overlapping free ends located at one of the cusps of the support frame. Preferably, there are identical indicators provided on each of the peaks in the middle of each valley around the annular element. The prosthetic heart valve has a labeled valve size, and the valve-type indicator may comprise a numerical value that equals, or a non-numeric symbol representative of, the labeled valve size in millimeters. The annular element desirably comprises a generally tubular metallic band that shows up as a positive image on the external imager, and the valve-type indicator is formed by one or more voids integrated into the band which show up as negative or positive images on the external imager.

The heart valve may further include an expandable tubular frame attached to an inflow end of the internal support frame on which a second valve-type indicator is located. The expandable tubular frame may comprise a series of circumferential and axial struts, wherein an upper strut is shaped with peaks and valleys around its periphery, and the valve-type indicator is integrated into the frame as a tag below the upper strut and along one of the axial struts.

Some embodiments provide a prosthetic heart valve, comprising: an internal support frame defining a flow orifice therethrough, the internal support frame is adapted for post-implant expansion; a plurality of flexible leaflets attached to the support frame and extending across the flow orifice and coming together within the orifice to define one-way flow therethrough; and a valve-type indicator that provides information about a characteristic of the heart valve, the valve-type indicator readable using an external imager.

Some embodiments provide a prosthetic heart valve, comprising: an internal support frame defining a flow orifice therethrough, the internal support frame defining a plurality of cusps that curve toward the inflow end separated by commissures, the support frame comprising an annular element disposed at an inflow end of the support frame that undulates so as to have peaks and valleys, with the peaks corresponding to the commissures of the support frame; a plurality of flexible leaflets attached to the support frame and extending across the flow orifice and coming together within the orifice to ensure one-way flow therethrough, each of the leaflets attaching at a peripheral edge along the cusps and commissures of the support frame; and an indicator comprising at least one feature in annular element at least a portion of the indicator having a radiopacity different from the radiopacity of the annular element, the indicator indicating a valve type and visible using an external imager. At least a portion of the annular element can be radiopaque, with the indicator including at least one opening extending through the at least one radiopaque portion of the annular element.

Some embodiments provide a method for replacing a prosthetic valve in need thereof, the method comprising: reading a valve-type indicator of a first prosthetic valve, selecting a second prosthetic valve based on the information read, and deploying the second prosthetic valve in the first prosthetic valve. Optionally, the method includes expanding a diameter of the first prosthetic valve prior to, contemporaneously with, or simultaneously with deploying the second prosthetic valve.

Other features and advantages of the present invention will become apparent from the following detailed description, taken in conjunction with the accompanying drawings which illustrate, by way of example, the principles of the invention.

BRIEF DESCRIPTION OF THE DRAWINGS

FIG. 6A is an elevational view of an alternative outer support band having a symbolic valve-size indicator thereon at one of the cusps of the band, and FIG. 6B is a key chart for decoding the meaning of the symbolic valve-size indicator;

FIG. 7 is an elevational view of a still further outer support band having a plurality of holes formed around its circumference whose number equals the valve size in millimeters;

FIG. 8A is an elevational view of another outer support band having a symbolic valve-size indicator thereon at one of the commissures, and FIG. 8B is a key chart for decoding the meaning of the symbolic valve-size indicator;

FIG. 9A is another outer support band having a symbolic valve-size indicator thereon at one of the commissures, and FIG. 9B is a key chart for decoding the meaning of the symbolic valve-size indicator;

DETAILED DESCRIPTION OF CERTAIN EMBODIMENTS

The prosthetic heart valves described herein each include an internal (meaning incorporated into the valve itself as opposed to being a supplemental element) stent or frame that is generally tubular in shape and defines a flow orifice area through which blood flows from an inflow end to an outflow end. Alternatively, the shape of the internal stent can be oval, elliptical, irregular, or any other desired shape. The valves preferably include flexible leaflets that selectively allow for fluid flow therethrough. Thus, the flow orifice area is alternatively open and closed via movement of leaflets. The heart valves may also include an outer or peripheral sewing or sealing ring formed of soft, suture-permeable material, which is typically used as an anchor to secure the valve to a native annulus, but can also be primarily for sealing against paravalvular leaking.

As referred to herein, the prosthetic heart valves used in accordance with the devices and methods of the invention may include a wide variety of different configurations, such as a prosthetic heart valve having one or more bioprosthetic tissue leaflets (e.g., bovine or porcine), a synthetic heart valve having polymeric leaflets, and in general any that are configured for replacing a native or previously implanted prosthetic heart valve. The prosthetic heart valves described herein are typically used for replacement of aortic, mitral, tricuspid, or pulmonic valves, but may also be used as a venous valve. These replacement prosthetic heart valves can also be employed to functionally replace stentless bioprosthetic heart valves.

In a preferred embodiment, internal valve stents or support frames disclosed herein have "expandable segments" that enable post-implant expansion. This can occur from the expandable segment rupturing, plastically stretching, and/or elastically elongating. Thus, an "expandable segment" means a location on the stent that enables it to enlarge in diameter, such as when a balloon is inflated within the stent. Examples include weak points which can rupture, thinned areas that rupture or stretch, accordion-like structures that elongate elastically or plastically, breaks in the stent that are held together with a breakable member such as a suture, weak link, or spot weld, and various other means. The term, "expandable segment" thus encompasses each and every one of these alternatives. For example, U.S. patent application Ser. No. 14/136,318, filed Dec. 20, 2013, and U.S. Patent Application Publication Nos. 2010/0076548 A1 and 2011/

0264207 A1 disclose various embodiments of expandable valves, the contents of which are expressly incorporated herein by reference.

Figures 1A, 1B, 1C, 1D, 1E:
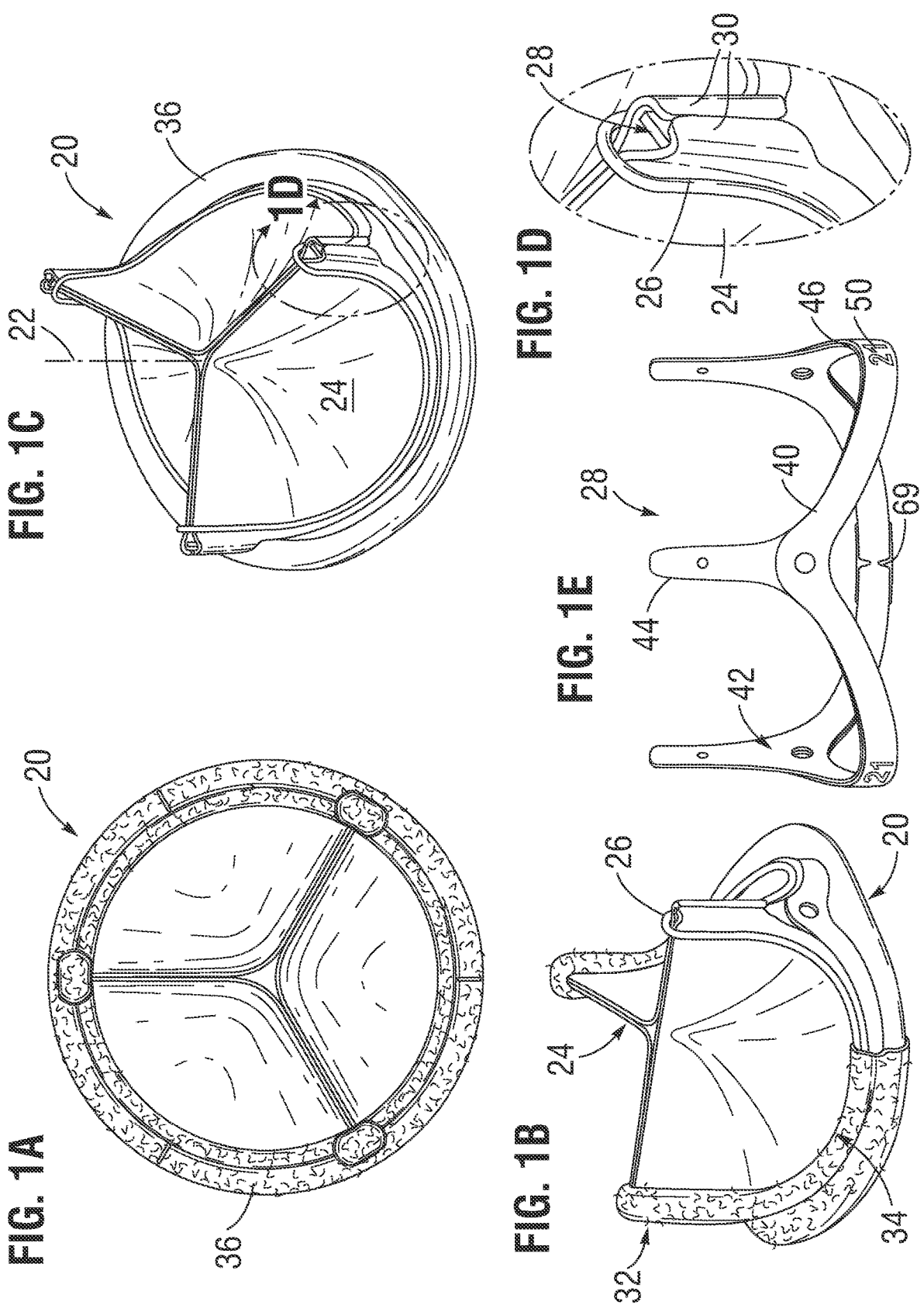
FIGS. 1A-1E are perspective and cutaway views of an exemplary surgical prosthetic heart valve of the present application having inner structural bands adapted for post-implant expansion and having valve-size indicators on an internal component visible from outside the body.

FIGS. 1A-1E are perspective and cutaway views of an exemplary prosthetic heart valve 20 of the present application oriented around a presumed flow axis 22. The heart valve 20 comprises a plurality of (usually three) flexible leaflets 24 supported partly by an undulating wireform 26 as well as by a structural stent 28 (FIG. 1E). The combination of the wireform 26 and the structural stent 28 define a support frame for the leaflets 24. The wireform 26 may be formed from a suitably elastic metal, such as a Co—Cr—Ni alloy (e.g., Elgiloy® alloy), while the structural stent 28 may be metallic, plastic, or a combination of the two. As seen best in FIG. 1B, the support structure of the wireform 26 and stent 28 define an undulating periphery of alternating commissures 32 and cusps 34 to which the leaflets 24 are secured. As seen in FIG. 1D, outer tabs 30 of adjacent leaflets 24 extend between adjacent wires at the commissures of the wireform 26 and wrap around a portion of the structural stent 28. This construction, covered with cloth and secured with sutures, forms the commissures 32 of the valve that project in an outflow direction along the flow axis 22. Each commissure 32 is located intermediate two arcuate cusps 34 that curve toward the inflow direction. A soft sealing or sewing ring 36 circumscribes an inflow end of the prosthetic heart valve 20 adjacent to and just radially outward from the cusps 34 and may be used to secure the valve to a native annulus, such as with sutures. The wireform 26 and structural stent 28 are visible in the cutaway views, and are normally covered with a polyester fabric as shown to facilitate assembly and to reduce direct blood exposure after implant.

FIG. 1E shows the inner structural stent 28, which in the illustrated embodiment includes an assembly of two concentric annular bands: an outer band 40 surrounding and in contact with an inner band 42. Although the indicators described herein can be utilized in a number of different prosthetic heart valves, the illustrated structural stent 28 is that used in a particular line of heart valves; namely, pericardial heart valves manufactured by Edwards Lifesciences of Irvine, CA. For example, the Perimount® heart valves that utilize pericardial leaflets 24 feature an inner stent 28 much like that shown in FIG. 1E. The annular support bands 40, 42 are relatively thin in a radial dimension as compared to an axial dimension, and have coincident lower edges that undulate axially up and down around the circumference. The outer band 40 exhibits three truncated peaks between three downwardly curved valleys, while the inner band 42 has generally the same shape but also extends upward at commissure posts 44. The downwardly curved valleys defined on both bands 40, 42, as seen in FIG. 1E, are typically termed cusps 46. Many commercial prosthetic heart valves include support frames with annular elements and those of skill in the art would understand that they could be modified to include the indicators of the present application.

In the exemplary Perimount® valves, the outer band 40 is metallic (such as Elgiloy® Co—Cr—Ni alloy) and is formed from an elongated strip of metal curved to the generally circular shape and having free ends that are welded together. In contrast, the outer band 42 is formed of a biocompatible polymer such as polyester (PET) or Delrin® polyacetal that may be molded, and also may be formed as a strip, circularized, and welded or bonded closed (not shown). Both the outer and inner bands 40, 42 typically feature a series of through holes that register with each other so that the assembly can be sewn together. The wireform 26 and the commissure posts 44 of the inner band 42 provide flexibility to the commissures of the valve, which reduces stress on the bioprosthetic material of the leaflets 24. The inflow end or base of the valve 20 surrounded by the sewing ring 36, however, comprises the relatively rigid circular portions of the structural stent 28. The combination of the metallic outer and plastic inner bands 40, 42 presents a relatively dimensionally stable circumferential base to the valve, which is beneficial for typical uses. These same characteristics of the structural stent 28 that provide good stability for the surgical valve resist post-implant expansion of the valve, however. Consequently, the structural stent 28 may be modified to facilitate expansion thereof for use in a valve-in-valve procedure.

The ability of a previously implanted prosthetic heart valve to expand is not always known. Indeed, the procedure is relatively new, and therefore most implanted valves have not been designed for radial expansion. Moreover, expandable valves that are now more frequently implanted may not be easily identified by a surgical team considering a valve-in-valve procedure. Although notes of each patient's surgery are taken at the time of each procedure, poor record-keeping, a lack of communication between doctors and hospitals, patient relocations to different states and even countries, the presence of an emergency, and other factors may make those records unavailable to a subsequent surgical team years later. Indeed, even information as seemingly straightforward as the size of the previously implanted prosthetic heart valve may not be readily available, and imaging from outside the body may not provide a precise determination of the valve size.

Consequently, the present application provides various solutions for easily identifying surgical heart valves in terms of size and type. In a preferred embodiment, at least the size of the heart valve is indicated on a component thereof in a manner that is visible from outside the body, post-implant. As used herein, "visible" includes the senses of "readable", "visualizable", "detectable", and "interpretable". For instance, FIG. 1E shows a size indicator 50 formed in each of the cusps 46 of the outer band 40. The valve-size indicator 50 may be formed by cutting holes or voids through the radiopaque outer band 40 (a negative or positive image), or by forming a band of non-radiopaque material and adding radiopaque indicators (a positive image). In some examples, all or a part of the indicator is defined by a thinner and/or a thicker region of the outer band, for example, by cutting or machining a design into but not through the outer band. The thickness variations are selected to provide a sufficient change in the radiopacity of the band to permit visualization of the indicator from outside the body. Some alternatives include through openings as well as thickness variations. Various alternative designs and encoding schemes are described below. The size indicator 50 in this example comprises the numeric characters "21" indicating that the valve orifice size is 21 mm. Heart valve sizes have been standardized for many years into millimeter increments starting at 19 mm and going up to 31 or 33 mm for larger patients. The present application describes valve-size indicators that follow this convention, although it should be understood that other sizing conventions may be used and thus the application should not be considered limited to these odd-millimeter-size increments. As for the term, "valve size," each prosthetic heart valve has a labeled size (e.g., between 19 and 33 mm in 2 mm increments) that denotes the valve size, and is of a particular valve model, such as a mitral valve of a particular type, which the valve packaging reflects.

Components within the prosthetic heart valves can also be coded so that they indicate whether the valve is expandable or not. It should be understood, however, that the valve-size indicators may also be used for non-expandable valves, as well as those that are capable of post-implant expansion. Any subsequent valve surgery benefits from knowledge of the size of the previously-implanted heart valve. Additional information on the previously-implanted valve, such as the manufacturer and/or model of the valve, and the valve's compatibility with other types of valves is also beneficial and can be encoded on the prosthetic heart valve as well.

Figures 2, 3, 4:
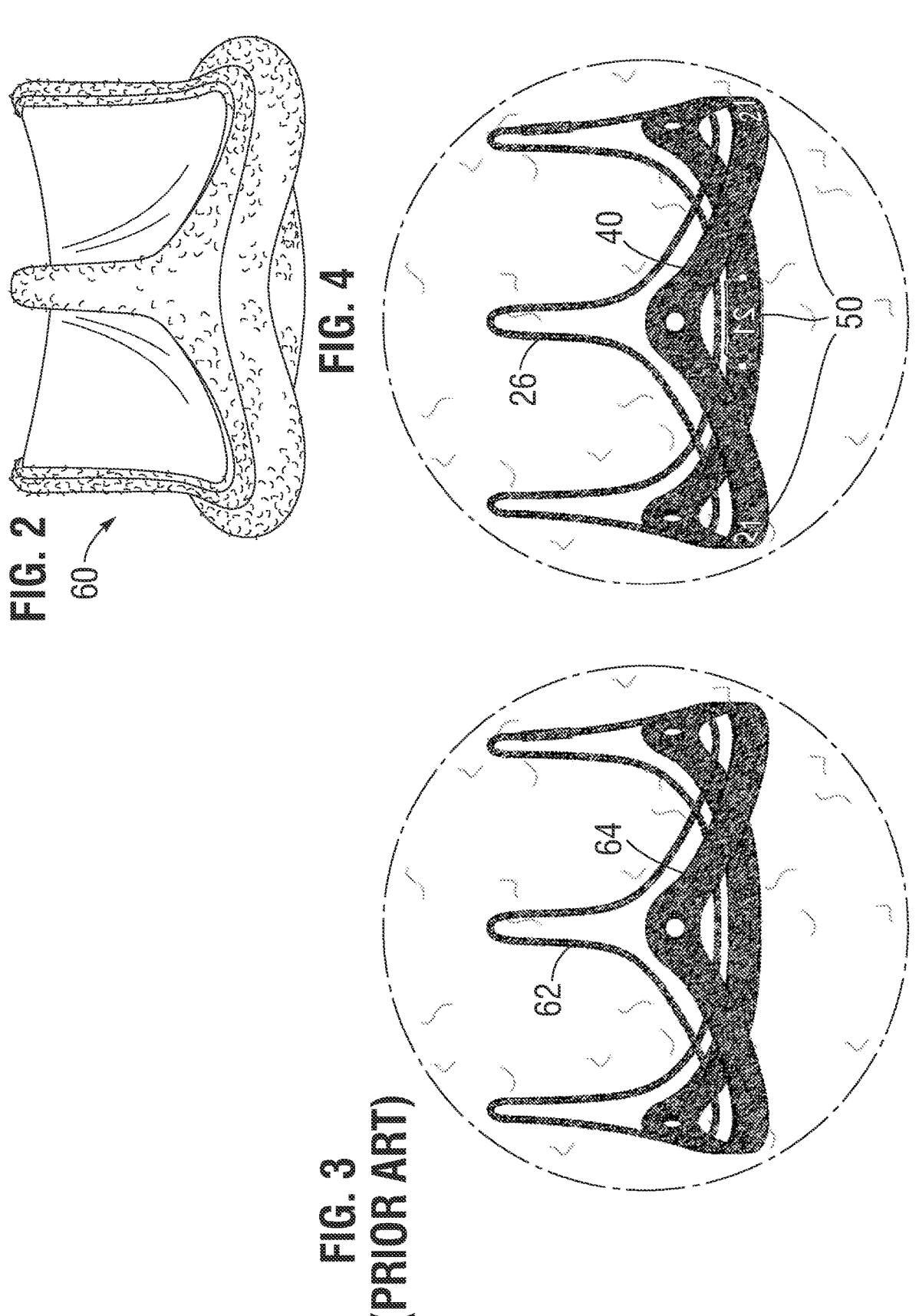
FIG. 2 is a side elevational view of an exemplary surgical prosthetic heart valve of the present application.
FIG. 3 is a schematic view of an image of a prosthetic heart valve of the prior art as seen using an X-ray or other imager from outside the body in the same orientation as FIG. 2.
FIG. 4 is a schematic image similar to that of FIG. 3 of a prosthetic heart valve of the present application having valve-size indicators on an internal frame component that are visible from outside the body using an X-ray or other imager.

FIGS. 2-4 illustrate the benefits of providing an indicator such as valve size on the surgical valve. Although different types of indicators are contemplated, for simplicity, only valve-size indicators will be described below. It is to be understood, however, that indicators that provide identifying information of any kind are part of the invention described herein. FIG. 2 is a side elevational view of an assembled surgical valve 60, which could be the exemplary valve 20 shown in FIGS. 1A-1E, but also represents a surgical valve without any indicators. That is, embodiments of the surgical valve 20 of the present application desirably have size indicators on one or more internal components that are visible using imaging but not to the naked eye. Of course, this does not preclude adding a radiopaque valve-size indicator to the exterior of the valve, but certain internal components as described herein are better suited for placement of the indicators. For example, integrating the indicators with structural elements of the valve permits a similar assembly procedure as for a non-indicator valve, as well as maintaining a similar part-count. Incorporating the indicators internally also does not materially affect the hemodynamics of the valve. Indeed, a valve-size indicator on the exterior of the valve that is visible to the naked eye is not precluded either, though such would not necessarily show up under imaging, post-implant.

FIG. 3 is a schematic view of an image of a prosthetic heart valve of the prior art as seen using an X-ray or other imager from outside the body in the same orientation as FIG. 2. The X-ray imager identifies those components within the heart valve, typically metallic, that block the X-ray spectrum radiation. In the embodiment shown, which is a surgical heart valve similar to that described above, the X-ray imager reveals an internal wireform 62 and a support band 64. Portions that block the X-ray beam will show up darker than other portions. The prior art valve of FIG. 3 has no size identifiers thereon, and thus a surgeon viewing the image would need to make an educated guess as to the particular valve size. Given that valves are produced with orifice sizes in only two millimeter increments, the task is somewhat difficult.

FIG. 4, on the other hand, is a screen shot of an X-ray image of the prosthetic heart valve 20 of FIGS. 1A-1E. Again the X-ray imager illuminates both the wireform 26 and outer band 40, however the valve-size indicators 50 also appear. That is, the indicators 50 comprise the numeral "21" which have been cut into each of the three cusps 46 of the band 40. Because the indicators 50 are provided at all three cusps, they is conveniently visible from different orientations. A surgeon can thus easily identify the valve size, 21 mm, and proceed accordingly. As will be described below, additional features may be provided on the radiopaque components of the prosthetic heart valve 20 that indicate its expandability and that would show up on an X-ray image as seen in FIG. 4.

The term "imager" for use from outside the body ("external imager") to detect the indicators includes any device capable of visualizing discrete elements inside the body from the outside, in general any device used in the fields of radiology that can produce such images. These fields include X-ray imaging or fluoroscopy which sees reflected X-rays, magnetic resonance imaging, medical ultrasonography or ultrasound, and nuclear medicine functional imaging techniques such as positron emission tomography. The term "imager" also includes devices or systems that include at least one component that is disposed within a patient's body, for example, an ultrasound emitter.

Figure 5A:
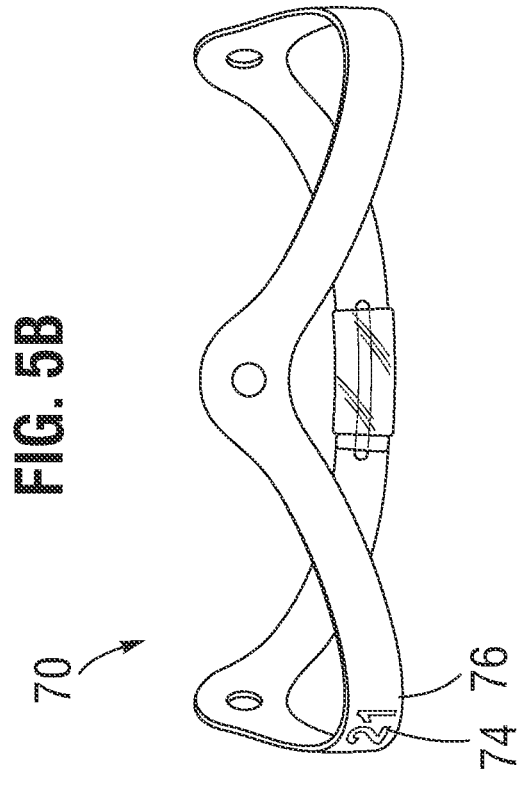
FIGS. 5A-5D are elevational views of different outer support bands for use in the valve of FIGS. 1A-1E with valve-size indicators thereon in various locations, the bands having overlapping free ends held together by a frictional sleeve to enable post-implant expansion.

As mentioned, various alternatives of the valve-size indicators are described herein. FIGS. 5A-5D are elevational views of outer support bands for use in the valve of FIGS. 1A-1E with valve-size indicators thereon in various locations. FIG. 5A shows the outer band 40 described above having the valve-size indicators 50 on all three of the cusps 46 thereof. Again, the valve-size indicators 50 comprise the "21" cut through the thickness of the metallic band 40 so that its image will show up in negative on X-ray in contrast with the dark "positive" reflected portions of the rest of the band. It should be noted that while the same indicator, in this case the valve size "21" mm, is shown at all three locations, different indicators can be used as well. Thus, different symbols providing different types of identifying information can be provided in the three different locations along the band. It should be understood that indicators may be located anywhere along the band and not only at the cusps and/or commissures, and that the band may include any number of indicators.

The outer band 40 comprises two overlapping free ends 66 held together by a frictional sleeve 68. This is one possible embodiment permitting expansion of the band 40, and thus the entire valve 20. More detail about this arrangement will be provided below. It should be noted however that the inner band 42 (FIG. 1E) also preferably includes an expansion feature at the same location where the outer band expands. Examples of suitable expansion features for the inner band include structures that expand or are easily ruptured. For example, as shown in FIG. 1E, the inner band 42 features a break point such as a notch 69 located at one cusp of 46 of the band structure. The notch 69 represents a reduced cross-sectional area that can be broken or stretched by applying sufficient outward expansion force from within. For example, a balloon used to expand a secondary prosthetic valve within the surgical valve can provide sufficient outward force to cause the inner band 42 to rupture or stretch at the notch 69. The material of the inner band 42 may be relatively brittle so that excessive tensile forces cause the notch 69 to break, or the material can be more ductile which permits the notch 69 to plastically stretch in the manner of taffy.

Figure 5B:
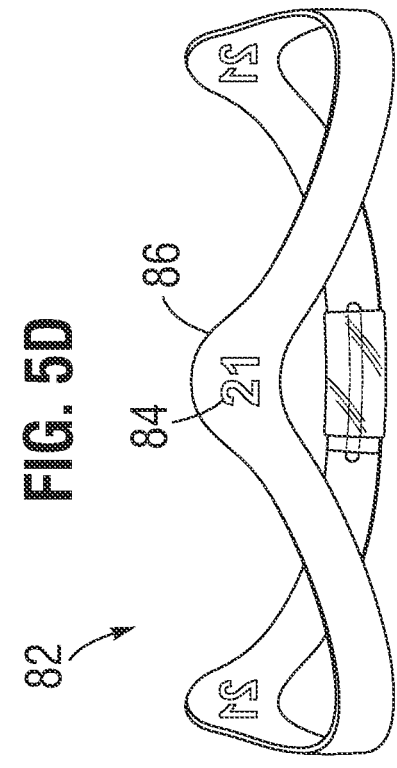
Figure 5C:
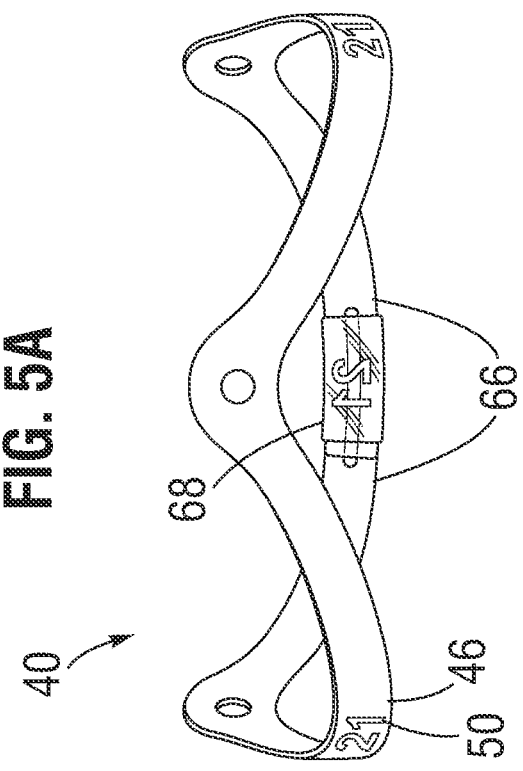
Figure 5D:
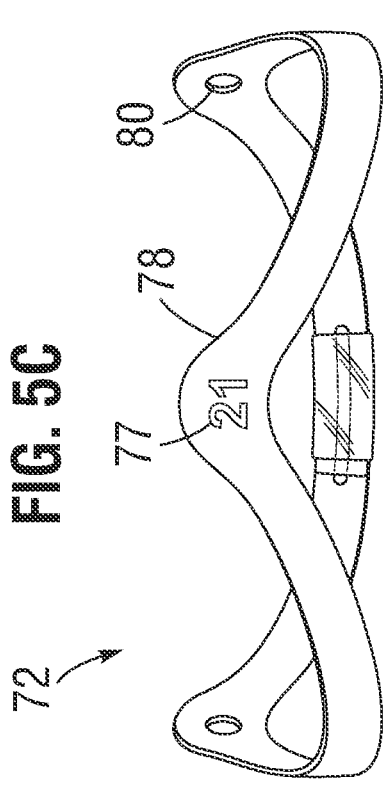

FIGS. 5B and 5C illustrate alternative outer bands 70, 72, respectively, which have single size indicators 74, 76 thereon. In the former case, a single size indicator 74 in the form of the numeral "21" is cut into one of the cusps 76 of the band 70. In the latter instance, the single size indicator 77 has been relocated to one of the truncated commissures 78 of the band 72. The valve-size indicators 74, 76 may be placed in either position, though slightly more material is available at the commissures 78. Furthermore, the size indicator 76 in the band 72 is cut entirely through the thickness of the band, and can function simultaneously as a substitute for the holes or openings 80 that are normally provided at the commissures to attach the outer band to an inner band with suture. FIG. 5D illustrates a band 82 similar to that shown in FIG. 5C, but where there are valve-size indicators 84 at each of the truncated commissures 86.

FIG. 6A illustrates a still further example of an outer support band 90 having a symbolic valve-size indicator 92 located at one of the cusps 94. In this case, the valve-size indicator 92 comprises a pair of geometric shapes cut into the band 90 that together indicate the valve size. FIG. 6B illustrates an exemplary key chart for decoding the meaning of the symbolic valve-size indicator 92 that would be provided along with the valve, and made available for use by surgeons seeking to decode the indicator, for example, on a webpage or other readily accessible location. For example, the first column of the key chart matches various geometric shapes with single digits, and corresponds to both the first or left indicator symbol and the digit in the first position of the valve size number. Likewise, the second column corresponds to the second or right indicator symbol and the digit in the second position of the valve size number. In the illustrated embodiment, the left indicator symbol is a circle, and the right indicator symbol is a square. Therefore, the digit in the first position of the valve size number corresponding to the circle is 2, and the digit in the second position of the valve size number corresponding to the square is 1, so that the indicated valve size is "21" or 21 mm. Using relatively large and simple geometric shapes that can be easily distinguished from one another upon imaging may be preferable to numeric characters which sometimes are subject to ambiguity (e.g., distinguishing a "1" from a "7"). Other schemes for encoding information are used in other embodiments, for example, a palindromic scheme that reads the same in either direction. In other schemes, the encoding is selected so that a string of characters read backwards is not mapped to the representation for a different size.

The term "voids" refers to numbers, holes, geometric or other symbols formed or cut into the radiopaque support bands described herein, or other radiopaque internal elements of a valve support frame. By cutting the void into an otherwise solid element, the indicator will show up as a negative image when visualized through an external imager. For example, the numeric characters "21" shown in the band 40 of FIG. 5A or the geometric shapes formed in the band 90 of the FIG. 6A comprise voids in the otherwise solid outer profile of the bands. Positive images may also be generated as well using appropriately shaped cut-outs. Some embodiments use a combination of positive and negative images, for example, to encode different types of information, and/or to unambiguously differentiate a first digit from a second digit.

FIG. 7 shows another outer support band 96 having a plurality of holes 98 formed around its circumference whose number equals the valve size in millimeters. That is, counting the number of holes or openings 98 provides the valve size. In the illustrated embodiment, although not all are shown, there are 23 holes such that the valve sizes 23 mm. The existing holes 99 at the commissures for attaching the bands together are desirably included in the count to avoid confusion. In any scheme, the openings need not be disposed equidistantly around the band. For example, some in some schemes, the positions around the band are assigned hierarchies, each of which is are filled before the next level. For example, in one scheme, the three positions at the commissures are filled first, followed by positions clockwise of the commissures, etc., so that the openings are grouped into three sets that can differ by at most 1 opening. Such a scheme facilitates determination of the precise number of openings.

FIG. 8A illustrates a further variation of outer support band 100 having a symbolic indicator 102 thereon at one of the commissures 104. In this instance, patterns of geometric shapes are cut that incorporate one of the existing suture holes to represent each size. FIG. 8B is a key chart for decoding the meaning of the symbolic valve-size indicator 102. In the illustrated embodiment, the pattern includes a square and two circles, which corresponds to 21 mm.

FIG. 9A is a still further outer support band 110 having a symbolic indicator 112 located at one of the commissures 114. In this embodiment, patterns of dots and dashes (similar to Morse code) again incorporating one of the existing suture holes are used to represent each valve size. FIG. 9B is a key chart for decoding the meaning of the symbolic valve-size indicator 112. The shapes cut into the commissure 114 included a dash and two dots, which corresponds to a size of 21 mm. The use of dashes and dots may be easier to decipher rather than trying to discern the different geometric shapes as in FIG. 8A.

Figure 10:
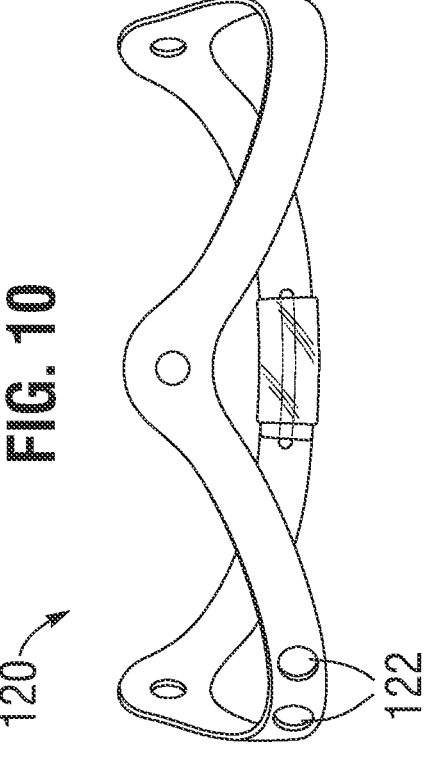
FIG. 10 is an elevational view of a still further outer support band having a plurality of holes provided on one of the cusps whose number symbolizes a particular valve size.

In FIG. 10, an outer support band 120 features a plurality of holes 122 provided on one of the cusps whose number symbolizes a particular valve size. Although not shown, a key chart could be provided to decode the symbol. However, typically heart valves start at 19 mm and go up by 2 mm increments, and thus the convention of using one dot for 19, two for 21, etc., may become well-understood. Therefore, the symbol shown, two holes 122, corresponds to about size of 21 mm, or the second smallest valve size. Likewise, three holes would correspond to a valve size of 23 mm, and so on. As discussed above, the hole or openings need not be adjacent, for example, may be distributed and/or grouped for more rapid identification.

Figure 11A:
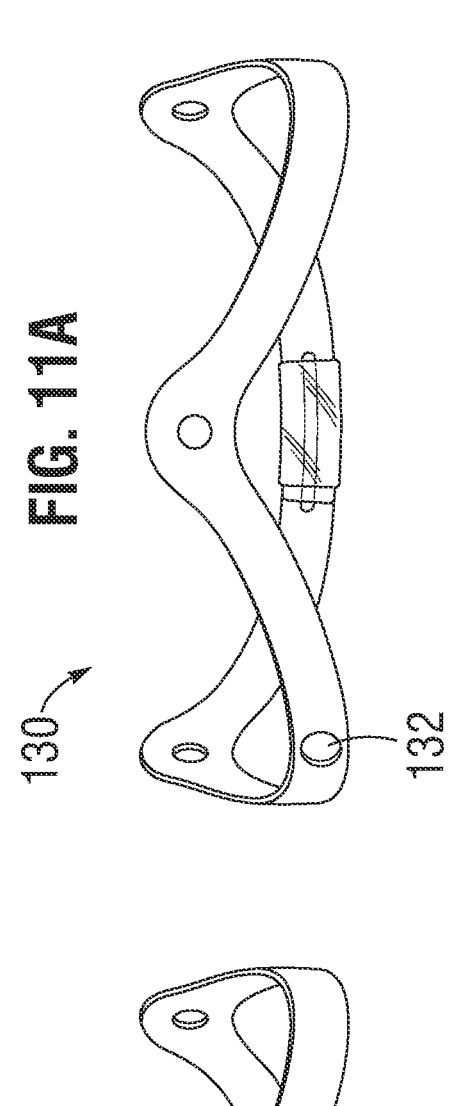
FIGS. 11A and 11B show support bands each having a single geometric symbol formed in at least one of the cusps that symbolizes a particular valve size.
Figure 11B:
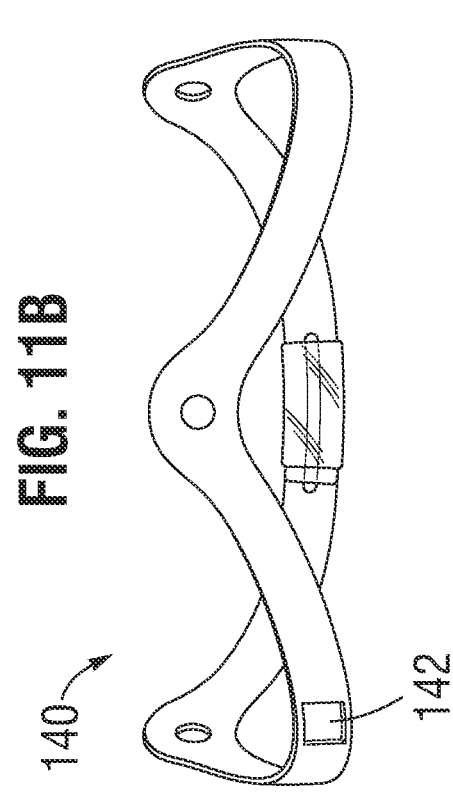

FIGS. 11A and 11B show support bands 130, 140, respectively, each having a single geometric symbol formed in at least one of the cusps that symbolizes a particular valve size. In particular, the band 130 in FIG. 11A features a symbol 132 in the form of a circle which might indicate a valve size of 19 mm, while the band 132 in FIG. 11B features a symbol 134 in the form of the square which might indicate a valve size of 21 mm. Again, a key chart might be provided, or the symbols may become generic in the industry such that surgeons will quickly recognize their meaning.

Figure 12:
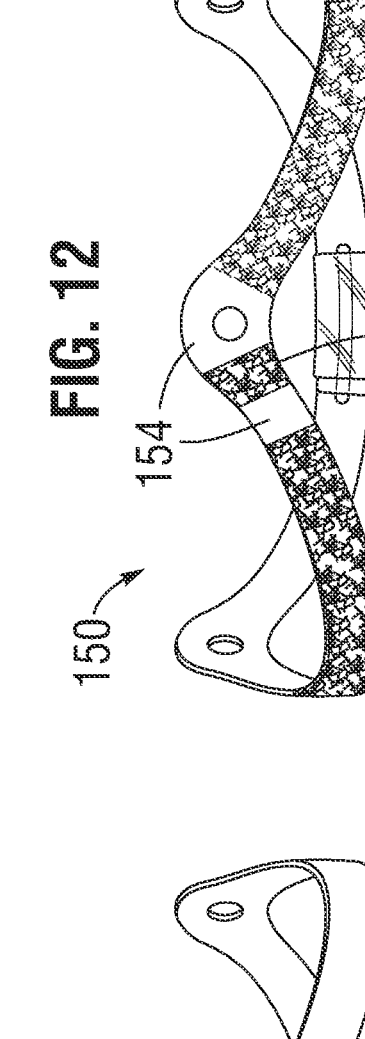
FIG. 12 is a still further outer support band having a radiopaque coating thereon in a pattern that symbolizes a particular valve size.

FIG. 12 illustrates an outer support band 150 having a radiopaque coating 152 thereon in a pattern that symbolizes a particular valve size. In the illustrated embodiment, the coating 152 extends entirely around the band 150 except for two gaps 154 that separate a single strip 156 from the rest of the coating. The number of gaps 154 indicates the valve size, in a similar manner to the number of holes 122 provided in the band 120 of FIG. 10. That is, the two gaps 154 in the illustrated embodiment correspond to a valve size of 21 mm, while a single gap would correspond to a smaller valve size of 19 mm and three gaps to 23 mm. In this embodiment, the material of the band 150 would not be intrinsically radiopaque, as opposed to the other bands described which are preferably metallic. For example, the band 150 might be formed of a relatively rigid polymer to provide the strength needed, but which does not show up on X-ray.

Figures 13A, 13B, 13C, 13D:
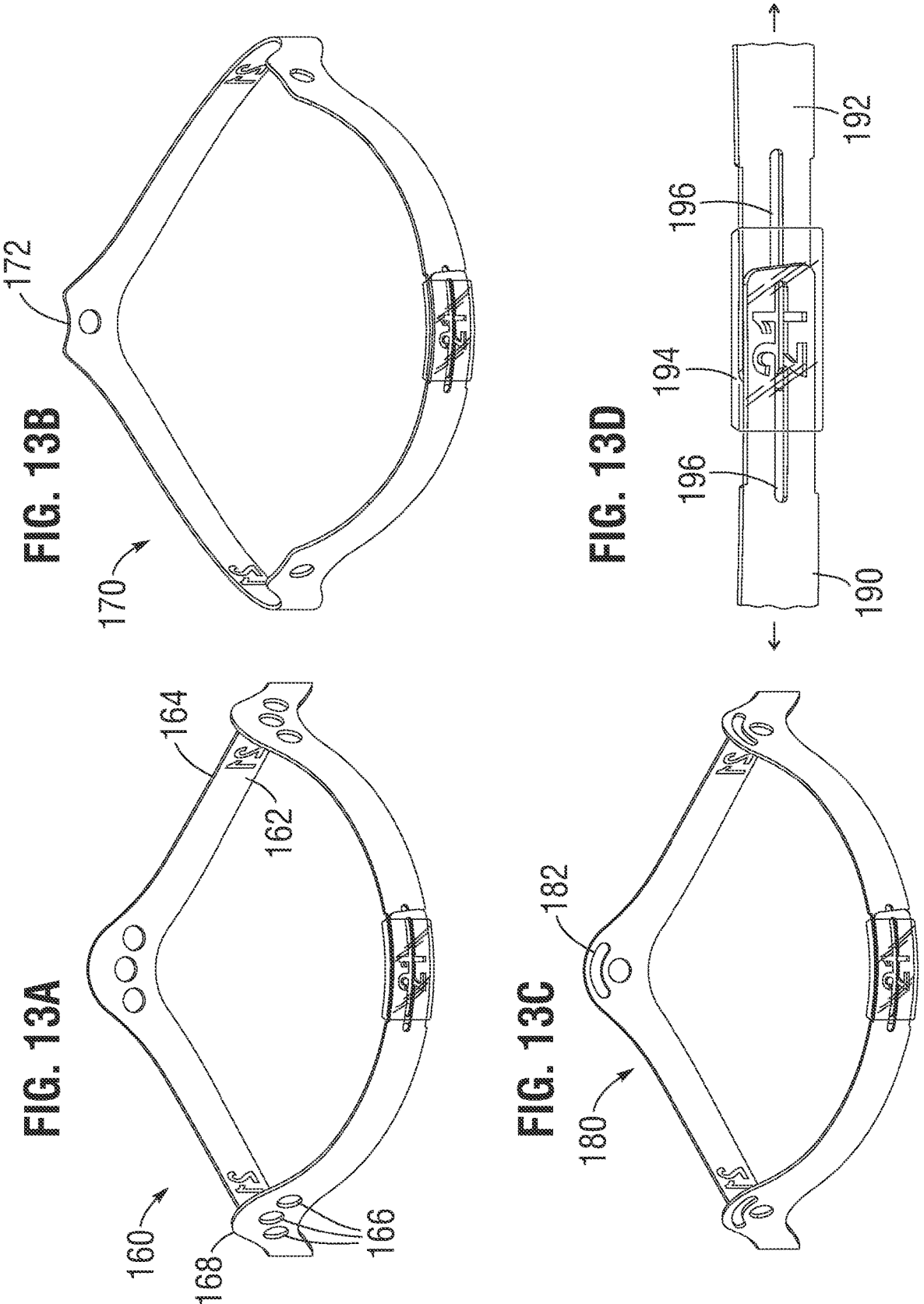
FIGS. 13A-13C are perspective views of a further prosthetic heart valve support band indicated for post-implant expansion and having overlapping free ends held together by a frictional sleeve.
FIG. 13D shows the expansion of the overlapping free ends.

FIGS. 13A-13C are perspective views of further prosthetic heart valve support bands capable of post-implant expansion with indicators thereon for both size and expansion capability. FIG. 13A shows a support band 160 having numerical valve-size indicators 162 at each cusp 164, and one or more symbols 166 visible using external imaging and indicating the capability for expansion at each commissure 168. In the illustrated embodiment the symbols 166 comprise a series of three holes that incorporate the existing suture hole that joins the inner and the outer bands together. This scheme permits a surgeon contemplating a replacement operation to quickly confirm that a valve-in-valve procedure is a possibility, and also confirm the existing implanted valve size.

FIG. 13B shows an outer band 170 having small depressions or concavities 172 formed at the peaks of the truncated commissures, which is distinct from the regular convex peaks such as those seen at the commissures of the bands described elsewhere herein. The concavities 172 indicate the capacity for valve expansion, post-implant. This alteration takes advantage of the relatively large surface area of the outer band 170 in the commissure areas without affecting valve function.

Finally, in FIG. 13C, a support band 180 again has the size indicators around its circumference so as to be readily identifiable in the body, post-implant, by external imaging. In contrast to the band 160, the support band 180 features an arcuate upwardly convex slot 182 at each commissure. Again, this indicator 182 may be easily visualized using external imaging, and clearly indicates to a surgeon that this particular valve is expandable and suitable for a valve-in-valve procedure.

FIG. 13D shows in detail the interaction between two overlapping free ends 190, 192 located at one cusp of any of the bands described herein that slide with respect to one another and permit expansion of the corresponding heart valve. The free ends 190, 192 are substantially rectangular in shape and one resides radially within and against the other. A sleeve 194 surrounds the free ends 190, 192 and holds them radially together. The sleeve 194 desirably comprises polyester (e.g., PET) shrink wrap tubing, or may be an elastic material, such as silicone rubber, and is shown transparent to illustrate the mating free ends 190, 192. The two free ends 190, 192 may slide apart a predetermined distance while still being overlapping. The flexible sleeve 194 provides a minimum amount of friction but generally serves to maintain alignment of the free ends 190, 192. Each of the free ends 190, 192 further includes a circumferentially-oriented slot 196 that stops short of the terminal ends and provides a pathway for fluid flow. The slots 196 extend farther outward from the sleeve 194 so that fluid can always enter the spaces within the sleeve. During storage, the slots 196 permit flow of a fluid between the overlapping free ends 190, 192 to allow for sterilization. With regard to break strength, the sleeve configuration in FIG. 13A-13B may require an average breaking pressure of about 1.2 atm, and within a range of from about 0.5 atm to about 2.0 atm. Further, the sleeve 194 may be biodegradable to maintain alignment of the two free ends 190, 192 for a period after implant and to then degrade to permit easy expansion of the band.

It should be noted here that the valve-type indicator, described herein as identifying an expandable valve, can also be used to provide further valve type information. For instance, the indicator may show what type of bioprosthetic tissue or other material is used in the valve, the valve manufacturer and/or model, the valve's compatibility with other valves, etc. Consequently, the term "valve type" refers to any valve-specific information, not just whether the valve is capable of expansion.

Figures 14A, 14B:
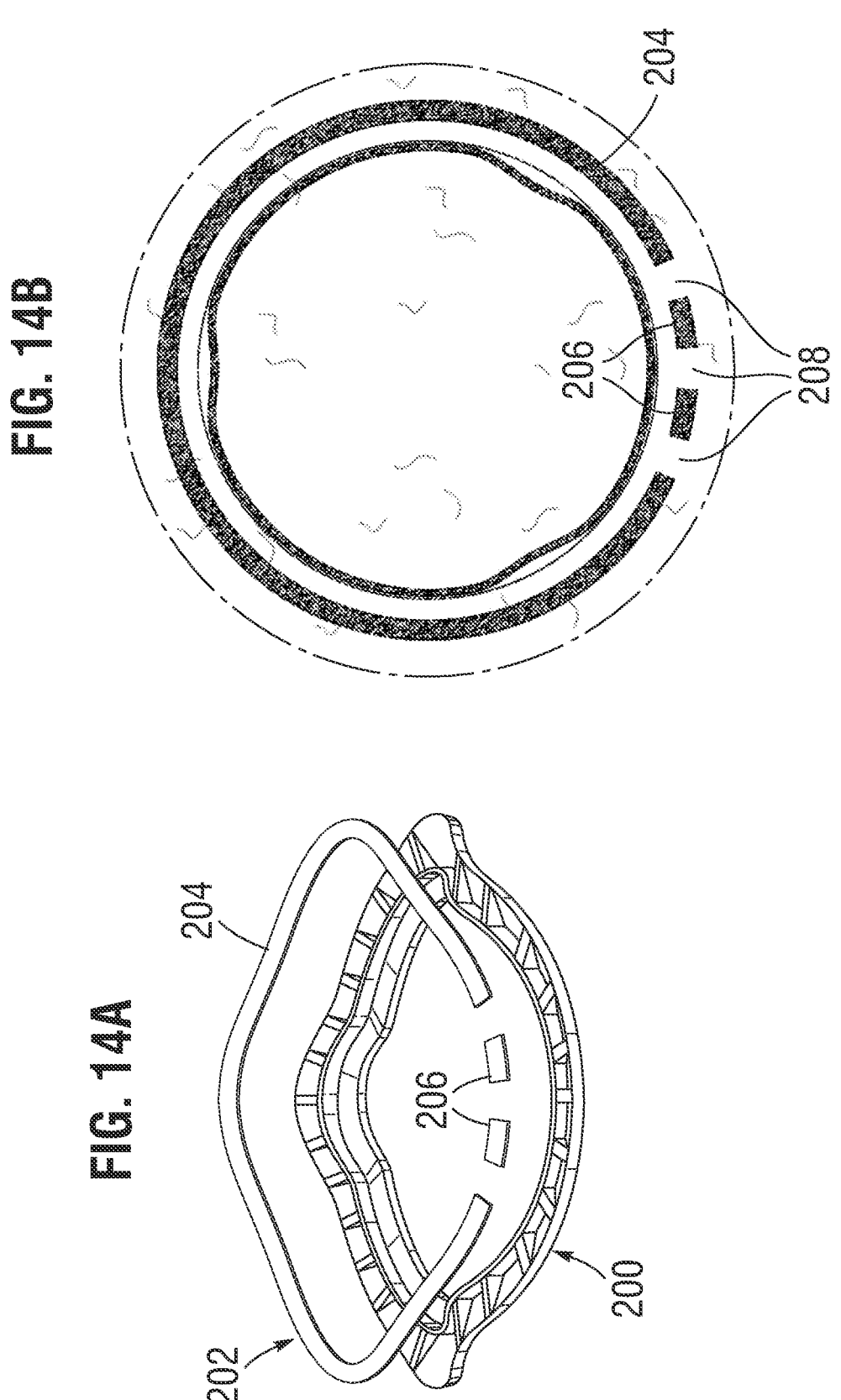
FIG. 14A is a perspective view of an inner core member of an exemplary sewing ring showing strips of radiopaque material exploded therefrom they can be incorporated into the sewing ring to indicate valve size.
FIG. 14B is a schematic top view as seen using an X-ray or other imager from outside the body of the valve having the radiopaque strips as indicated in FIG. 14A.

FIG. 14A is a perspective view of an inner core member 200 of an exemplary sewing ring for use in a heart valve as described herein with strips of radiopaque material 202 shown exploded above that can be incorporated into the sewing ring to indicate valve size. In the illustrated embodiment, the strips of radiopaque material 202 are provided in a single elongated strip 204, and two relatively short strips 206. By assembling these strips 204, 206 against the core member 200, which is typically covered with a biocompatible fabric prior to assembly with the rest of the heart valve, they can be visualized using external imaging to indicate the valve size. For example, FIG. 14B is a schematic top view as seen using an X-ray or other imager from outside the body of the valve having the radiopaque strips 204, 206 as indicated in FIG. 14A. The strips 204, 206 show up dark surrounding the similarly dark metallic components of the valve (annular), and can be interpreted to determine the valve size. For instance, the two short strips 206 create three gaps 208 around the sewing ring which might represent a valve size of 23 mm (one gap equals 19 mm, two gaps equal 21 mm, etc.). Alternatively, radiopaque beads can be used as indicators. This embodiment represents numerous other ways in which the valve size can be coded into the valve using any of the internal valve components, whether intrinsically radiopaque or not. Some embodiments use a combination of radiopaque strips or beads in the sewing ring and cutouts in the band, which permits encoding additional information and/or redundant encoding of more important information.

Figures 15A, 15B, 15C, 16:
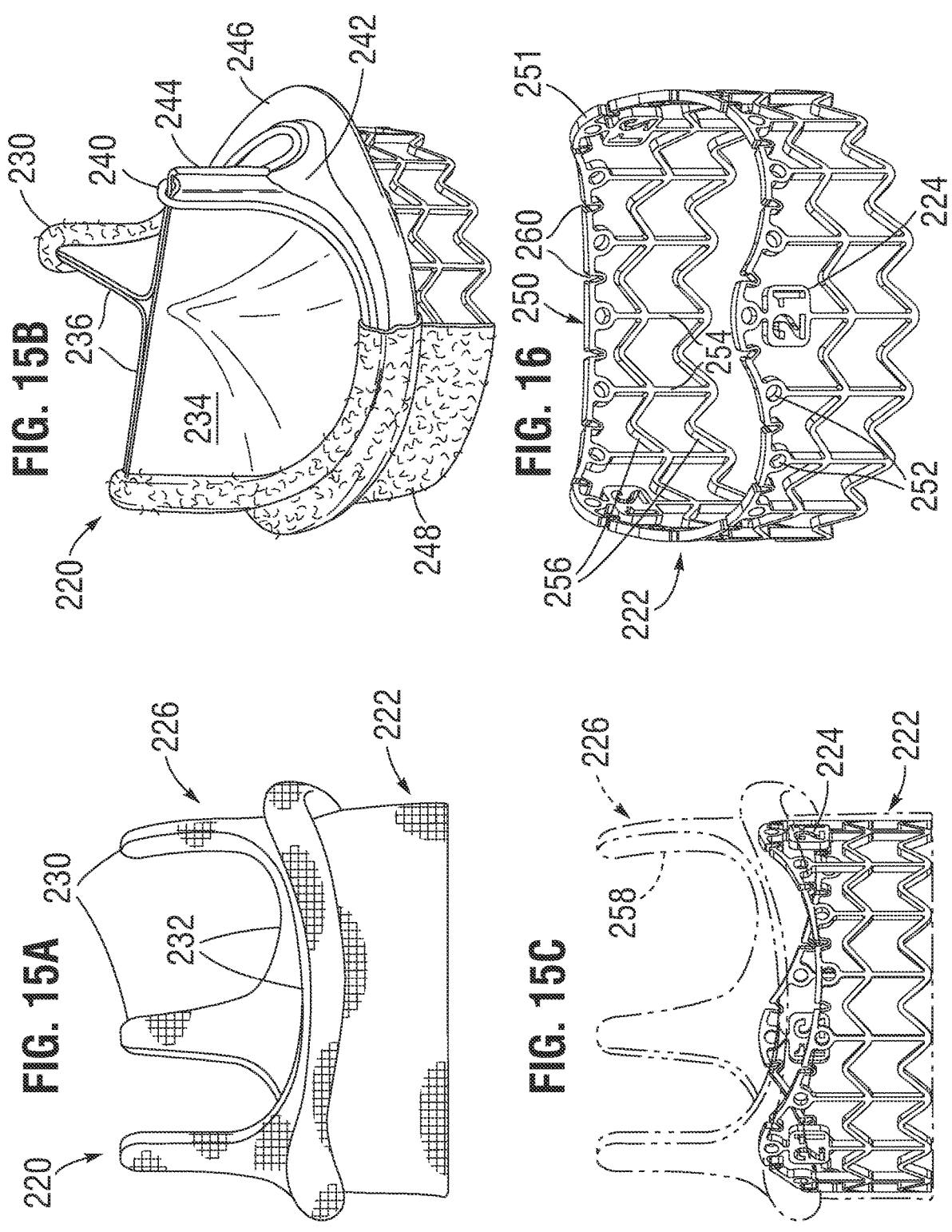
FIGS. 15A-15C are perspective and elevational views, some cutaway and phantom, of an exemplary prosthetic heart valve of the present application having an expandable lower frame with valve-size indicators thereon.
FIG. 16 is a perspective view of the lower frame with valve-size indicators of FIGS. 15A-15C.

FIGS. 15A-15C illustrate a further surgical prosthetic heart valve 220 of the present application having an expandable lower frame 222 with valve-type indicators 224 disposed thereon. The heart valve 220 includes an upper valve portion 226 connected to the lower frame 222. The valve-type indicators 224 may be on the upper valve portion 226 or lower frame 222, or both. In a preferred embodiment, the heart valve 220 and the frame 222 are capable of expansion to enable a valve-in-valve procedure as described elsewhere herein. The lower frame 222 is designed to expand during the original implant of the valve 220, while both the valve portion 226 and the frame 222 expand during a subsequent valve-in-valve procedure. That is, the upper valve portion 226 is not intended to expand and functions much like a typical non-collapsible/non-expandable surgical valve during original implant and functioning, but include features that permit a limited amount of expansion when subjected to large radial, outward forces from within, such as from expanding a balloon. The lower frame 222 may be made of a plastically-expandable material such as stainless steel or cobalt-chromium alloy, or a self-expandable material such as nitinol.

The upper valve portion 226 desirably includes a peripheral internal support frame, partially shown in the cutaway of FIG. 15B, which defines three upstanding commissure posts 230 alternating with three arcuate cusps 232. The commissure posts 230 project in an outflow direction and support outer edges of three flexible leaflets 234, shown in FIG. 15B but removed in FIG. 15A for clarity. The leaflets 234 are desirably separate bioprosthetic leaflets; for instance being cut from sheets of treated bovine pericardium, and each features an arcuate cusp edge that attaches along one of the arcuate cusps of the support frame, and two commissure edges or tabs that attach up adjacent commissure posts 230. A free edge 236 of each leaflet is suspended between the adjacent commissure posts 230 and comes into contact, or coapts, with the free edges of the other leaflets in the flow orifice defined within the peripheral support frame to form the one-way flow valve.

In a preferred embodiment, the support frame is defined partly by an undulating wireform 240 that defines the commissure posts 230 and extends around a generally tubular area and a structural stent 242 that may comprise annular bands; the parts similar to those shown at 62 and 64 in FIG. 3. The wireform 240 may be formed from a suitably elastic metal, such as a Co—Cr—Ni alloy, for example, Elgiloy® alloy, while the structural stent 242 may be metallic, plastic, or a combination of the two. As seen in FIG. 15B, outer tabs 244 of adjacent leaflets 234 extend underneath the wireform 240 and wrap around a portion of the structural stent 242 at the commissure posts 230. A soft sealing or sewing ring 246 circumscribes an inflow end of the prosthetic heart valve 130 and is typically used to secure the valve to a native annulus such as with sutures. The wireform 240 and structural stent 242 of the support frame are partially visible in the cutaway of FIG. 15B, and are normally covered with a polyester fabric 248 to facilitate assembly and to reduce direct blood exposure after implant.

The prosthetic heart valve 220 is considered a "hybrid" type in that it includes the upper valve portion 226 constructed similar to typical surgical valves, with a relatively stable diameter that is not normally intended to be compressed or expanded, while the connected lower frame 222 is expandable to help in anchoring the valve in place. One specific commercial prosthetic heart valve that is constructed in this manner is one which is sold in conjunction with the Edwards Intuity® valve system from Edwards Lifesciences of Irvine, CA. The Edwards Intuity® valve system comprises a "hybrid" valve incorporating a surgical Perimount®-like valve with a stainless steel lower frame structure. In contrast to a typical Edwards Intuity® valve, however, the valve portion 226 is modified in any of the manners described herein to permit post-implant expansion for use in a valve-in-valve procedure. Further, the heart valve 220 includes a size indicator to facilitate such a procedure.

With specific reference to FIG. 16, which illustrates the lower frame 222 in perspective, the lower frame 222 includes a plurality of circumferential row struts connected by a series of spaced axial column struts. Specifically, an upper or outflow row strut 250 extends continuously around a periphery of the frame 222, and preferably follows a gently undulating path so as to match a similar shape of the underside of the upper valve portion 226. As seen in FIG. 15C, three peaks 251 along the upper row strut 250 correspond to the locations of the commissures 230 of the valve 220, where the stent 242 rises upward as well. In general, the lower frame 222 attaches to an inflow end of the upper valve portion 226, and preferably directly to the internal support frame or to fabric covering the internal support frame. The lower frame 222 is generally tubular in the drawings, and on deployment, expands to be somewhat frustoconical with the free end farthest from the upper valve portion 226 expanding outward but the end closest remaining about the same diameter. Optionally, the lower frame is pre-crimped into a generally conical shape with the free end having a smaller diameter than the upper row strut 250, which is not substantially radially compressed.

The upper row strut 250 includes a plurality of eyeholes 252, evenly spaced apart in the illustrated embodiment, and located just below the top edge thereof that are useful for securing the frame 222 to the fabric of the underside of the valve portion 226, for example, using suture. A series of axial column struts 254 depend downward from the upper row strut 250, and specifically from each of the eyeholes 252, and connect the upper row strut to two lower row struts 256. The lower row struts 256 circumscribe the frame 222 in zig-zag patterns, with an inverted "V" shape between each two adjacent column struts 254. The lower row struts 256 preferably extend horizontally, and the length of the column struts 254 thus varies with the undulating upper row strut 250.

As mentioned above, the lower frame 222 may be plastically expanded, such as by balloon expansion, and may be formed of stainless steel or cobalt-chromium alloy, for example. In a typical Edwards Intuity® valve, the upper row strut 250 is generally ring-like without capacity for expansion. In the illustrated frame 222, on the other hand, a series of spaced notches 260 are provided that permit expansion. That is, circumferential segments of the strut 250 are interrupted by the V-shaped notches 260 which permits a limited amount of expansion, for example, about 3 mm in diameter, to accommodate a supplemental expandable valve to be inserted and expanded therein.

In addition, a number of valve-type indicators 224 are integrated into the frame 222 at locations around its circumference, such as three valve-size indicators. In the illustrated embodiment, the valve-size indicators 224 comprise small plate-like tags inscribed with the numerical valve size in mm, for example 21 mm in the illustrated embodiment. The use of any combination of alphanumeric characters and/or symbols that signify size and/or other features of the valve is contemplated. The frame 222 may be laser cut from a tubular blank, with the plate-like size indicators 224 left connected to one more of the struts. As shown, the size indicators 224 are located just below the peaks 251 of the undulating upper row strut 250, connected between the corresponding eyehole 252 and the descending column strut 254. There are thus three size indicators 224 spaced about 120° apart around the frame 222. The illustrated location beneath the peak 251 provides additional space between the upper row strut 250 and the adjacent lower row strut 256. Further, the frame 222 typically has more real estate in which to place the size indicators 224 than the bands of the valve portion 226. The inscribed or cutout valve size numerals are sufficiently large to be visualized with X-ray, Transesophageal Echocardiogram (TEE), or other imaging technique. In one embodiment, the valve size numerals are from about 1.5 mm to about 2 mm in height, for example, about 1.75 mm.

It should be understood that instead of the numerical valve-size indicators cut into the tags, any of the above-referenced size indicators may also be used in the same place. It is especially useful where the indicators are integrated into existing structures rather than being separate add-ons that require a separate attachment step. This not only reduces assembly time and cost, but also ensures the indicators are located at the ideal location for visualization, without requiring an alignment procedure. For instance, the various indicators disclosed herein are laser cut or stamped into the respective metallic parts, or distinguished by providing reflective coatings and the like on the parts.

Note that there are many variations of the above-described embodiments, including numerous combinations of the various embodiments, all of which are in the scope of the invention. For instance, the various numeric and symbolic indicators of valve size or valve type could be provided as radiopaque additions to the sewing ring, or in general mixed and matched as deemed necessary. Also, a particular support structure could have any combination of the above-discussed expandable portions.

As previously described, the at least one size indicator can be made of any suitable material, e.g., radiopaque or radiopaque impregnated material. The radiopaque material selected for this purpose may be biocompatible. Such materials include stainless steel, tungsten, tantalum, platinum, gold, barium silicate, as well as alloys such as cobalt-chromium (e.g., Elgiloy® alloy) or high-performance nickel alloys (e.g., Hastelloy® alloys).

Various processes exist for forming the radiopaque markers from such materials. In some embodiments, an etching process can be used to create the articles of the markers. This process may be a photo etching process whereby a photo-resistive coating is applied as a mask to a light-sensitive polymer plate. Light is projected onto the plate and the plates are then washed to remove the photo-resistive material that was used as the mask. An additional washing step may then be used to chemically remove the portion of the metal that was exposed to the light. In other embodiments, the photo-resistive coating and the exposed metal can be removed in one washing step. Other similar etching processes may be used as are known to those skilled in the art.

Another mechanism for creating the radiopaque articles for use in the described markers involves punching the articles from a sheet of radiopaque material. For instance, a ribbon of material may be fed into a die set having male and female portions that stamp out the characters. With a punching process, any rough edges and/or burrs generated thereby may need to be removed, polished, or cleaned.

Yet another technique for producing the radiopaque articles involves using a laser cutting technique, as mentioned. Laser cutting can produce very tight tolerances and smooth edges, aiding readability of small radiopaque markers. Some materials, however, may be expensive or difficult to process using this technique. In particular, this technique may be expensive at higher volume production levels.

Still another option for creating the radiopaque articles involves a sintering process. According to this technique, powdered radiopaque material mixed with glue is pressed into a form and baked until all of the glue has been dissipated and the radiopaque particles bind together. This type of process creates a porous structure which may more readily adhere to the molecules of a polymer used during a subsequent molding process, with the degree to which the polymer is received by the pores being dependent upon molecular size of the polymer.

Metal injection molding can also be used to create the radiopaque articles. In this scenario, a radiopaque powder or slurry is injected under pressure into a mold. The powder or slurry is then baked until the radiopaque particles bind one to another. As with sintering, this may produce a relatively more porous radiopaque article.

A prosthetic valve may lose effectiveness or fail for any number of reasons, for example, stenosis, pannus growth, regurgitation, and/or mechanical failure. Under such circumstances, replacement may be desirable. One option is to remove the failing prosthetic valve, for example, surgically, and to implant a new prosthetic valve in its place, Another option is to perform what-is-known as a valve-in-valve procedure in which a new valve is implanted into the failing valve without removal thereof. Where the new valve is a transcatheter valve, the procedure may be performed using minimally invasive procedures that are less traumatic to the patient. Although the failing valve is not actually removed, the procedure is often referred to as a "replacement" because the new prosthetic valve replaces the function of the failing valve.

An embodiment of a method for replacing a first prosthetic valve in need thereof with a second prosthetic valve includes reading a valve-type indicator of the first prosthetic valve, selecting a second prosthetic valve based on the information read, and deploying the second prosthetic valve in the first prosthetic valve. The first prosthetic valve includes any prosthetic valve including a valve-type indicator, including any of the embodiments described herein. The valve-type indicator can be of any type or combination of types described herein, for example, size, expandability, make, model, or any other information desired. The valve-type indicator is read, imaged, or visualized as described above.

Optionally, a diameter of the first prosthetic valve is expanded, for example, either immediately before, contemporaneously with, or simultaneously with the deployment with the second prosthetic valve. In some examples, the first prosthetic valve is expanded mechanically, for example, using a balloon, before the second prosthetic valve is deployed. In other examples, the deployment of second prosthetic valve itself expands the diameter of the first prosthetic valve. In some embodiments, the second prosthetic valve is a transcatheter heart valve, for example, a balloon expandable or self-expandable transcatheter heart valve. Optionally, the second valve is expanded post-deployment to improve engagement between the first valve and the second valve.

While the invention has been described with reference to particular embodiments, it will be understood that various changes and additional variations may be made and equivalents may be substituted for elements thereof without departing from the scope of the invention or the inventive concept thereof. In addition, many modifications may be made to adapt a particular situation or device to the teachings of the invention without departing from the essential scope thereof. Therefore, it is intended that the invention not be limited to the particular embodiments disclosed herein, but that the invention will include all embodiments falling within the scope of the appended claims.

What is claimed is:

1. A surgical prosthetic heart valve configured for open heart surgical implantation having a labeled valve size selected from a range, in 2 mm increments, between 19 and 33 mm, comprising:

a support frame defining a flow orifice therethrough, and the flow orifice has a diameter equal to the labeled valve size, the support frame defining a dimensionally stable circumferential base modified to permit a limited amount of post-implant expansion when subjected to radial outward forces from within;

a peripheral sewing ring around the circumferential base formed of suture-permeable material and configured for anchoring the valve to a native annulus using sutures;

a plurality of leaflets ensuring one-way flow through the flow orifice; and a valve-size indicator on the support frame indicating the labeled valve size, and a valve-type indicator on the support frame that signifies the capability of the support frame for post-implant expansion.

2. The heart valve of claim 1, wherein the support frame defines a plurality of cusps that curve toward an inflow end of the valve separated by commissures that project toward an outflow end of the valve, each of the leaflets attaching at a peripheral edge along the cusps and commissures of the support frame.

3. The heart valve of claim 2, wherein the support frame comprises a tubular band with a diameter that is expandable post-implant, and the valve-size indicator is located on the tubular band.

4. The heart valve of claim 3, wherein there are a plurality of valve-size indicators each aligned with a commissure of the support frame.

5. The heart valve of claim 1, wherein the valve-size indicator comprises a numerical value that equals the labeled valve size in millimeters.

6. The heart valve of claim 1, wherein the valve-size indicator comprises a non-numeric symbol.

7. The heart valve of claim 3, wherein the tubular band shows up as a positive image on an external imager, and the valve-size indicators are each formed by one or more voids integrated into the tubular band which show up as negative images on the external imager.

8. The heart valve of claim 1, wherein the support frame comprises a structural component that shows up as a positive image on an external imager, and the valve-size indicator is formed by one or more voids integrated into the structural component which show up as negative images on the external imager.

9. The heart valve of claim 1, wherein there are a plurality of valve-size indicators distributed around the support frame and each comprises a numerical value.

10. The heart valve of claim 1, wherein there are a plurality of valve-size indicators distributed around the support frame and each comprises a non-numeric symbol.

11. A surgical prosthetic heart valve configured for open heart surgical implantation having a labeled valve size selected from a range, in 2 mm increments, between 19 and 33 mm, comprising:

an expandable support frame defining a flow orifice therethrough, and the flow orifice has a diameter equal to the labeled valve size, the support frame defining a dimensionally stable circumferential base adapted to permit a limited amount of post-implant expansion when subjected to radial outward forces from within;

a peripheral sewing ring around the circumferential base formed of suture-permeable material and configured for anchoring the valve to a native annulus using sutures;

a plurality of leaflets ensuring one-way flow through the flow orifice; and a valve-type indicator on the support frame that signifies the capability of the support frame for post-implant expansion.

12. The heart valve of claim 11, wherein the prosthetic heart valve also has a valve-size indicator indicating the labeled valve size.

13. The heart valve of claim 11, wherein the support frame defines a plurality of cusps that curve toward an inflow end of the valve separated by commissures that project toward an outflow end of the valve, each of the leaflets attaching at a peripheral edge along the cusps and commissures of the support frame.

14. The heart valve of claim 13, wherein the support frame comprises a tubular band with a diameter that is expandable post-implant, and the valve-type indicator is located on the tubular band.

15. The heart valve of claim 14, wherein there are a plurality of valve-type indicators each aligned with a commissure of the support frame.

16. The heart valve of claim 12, wherein the valve-size indicators each comprise a numerical value that equals the labeled valve size in millimeters.

17. The heart valve of claim 15, wherein the tubular band shows up as a positive image on an external imager, and the valve-type indicators are each formed by one or more voids integrated into the tubular band which show up as negative images on the external imager.

18. The heart valve of claim 11, wherein the support frame comprises a structural component that shows up as a positive image on the external imager, and the valve-type indicator is formed by one or more voids integrated into the structural component which show up as negative images on the external imager.

19. The heart valve of claim 11, wherein there are also a plurality of valve-size indicators distributed around the support frame and each comprises a numerical value that equals the labeled valve size in millimeters.

20. The heart valve of claim 11, wherein there are also a plurality of valve-size indicators distributed around the support frame and each comprises a non-numeric symbol.

21. The heart valve of claim 11, wherein the support frame comprises a tubular band, and the valve-type indicator is formed in the tubular band and selected from the group consisting of a series of holes, a concavity and a slot.

22. The heart valve of claim 12, wherein the valve-size indicator is formed by strips of radiopaque material incorporated into the sewing ring.

23. The heart valve of claim 1, wherein the support frame comprises a tubular band, and the valve-type indicator is formed in the tubular band and selected from the group consisting of a series of holes, a concavity and a slot.

* * * * *